(12) United States Patent
Cerier

(10) Patent No.: US 8,092,472 B2
(45) Date of Patent: Jan. 10, 2012

(54) METHODS AND DEVICES FOR ENDOSCOPIC TREATMENT OF ORGANS

(76) Inventor: Jeffrey C. Cerier, Franklin, MA (US)

( * ) Notice: Subject to any disclaimer, the term of this patent is extended or adjusted under 35 U.S.C. 154(b) by 854 days.

(21) Appl. No.: 12/034,661

(22) Filed: Feb. 21, 2008

(65) Prior Publication Data
US 2008/0208216 A1    Aug. 28, 2008

Related U.S. Application Data

(60) Provisional application No. 60/891,057, filed on Feb. 22, 2007.

(51) Int. Cl.
  *A61B 17/10* (2006.01)
(52) U.S. Cl. .................... 606/139; 606/144; 606/232
(58) Field of Classification Search .................... 606/139, 606/144–157, 232
  See application file for complete search history.

(56) References Cited

U.S. PATENT DOCUMENTS

| | | | |
|---|---|---|---|
| 4,235,238 A * | 11/1980 | Ogiu et al. | 606/145 |
| 5,297,536 A | 3/1994 | Wilk | |
| 5,403,326 A | 4/1995 | Harrison et al. | |
| 5,792,153 A | 8/1998 | Swain et al. | |
| 5,904,147 A * | 5/1999 | Conlan et al. | 128/899 |
| 6,113,609 A | 9/2000 | Adams | |
| 6,238,335 B1 | 5/2001 | Silverman et al. | |
| 6,254,598 B1 | 7/2001 | Edwards et al. | |
| 6,554,845 B1 | 4/2003 | Fleenor et al. | |
| 6,663,639 B1 | 12/2003 | Laufer et al. | |
| 6,740,082 B2 | 5/2004 | Shadduck | |
| 6,773,440 B2 | 8/2004 | Gannoe et al. | |
| 6,773,441 B1 | 8/2004 | Laufer et al. | |
| 6,821,285 B2 | 11/2004 | Laufer et al. | |
| 6,845,776 B2 | 1/2005 | Stack et al. | |
| 6,911,034 B2 * | 6/2005 | Nobles et al. | 606/144 |
| 6,949,888 B2 | 9/2005 | Ribarich | |
| 6,966,919 B2 | 11/2005 | Sixto, Jr. et al. | |
| 6,981,978 B2 | 1/2006 | Gannoe | |
| 7,008,419 B2 | 3/2006 | Shadduck | |
| 7,037,344 B2 | 5/2006 | Kagan et al. | |
| 7,125,413 B2 | 10/2006 | Grigoryants et al. | |
| 7,153,314 B2 | 12/2006 | Laufer et al. | |
| 7,175,638 B2 | 2/2007 | Gannoe et al. | |
| 7,214,233 B2 | 5/2007 | Gannoe et al. | |
| 7,220,237 B2 | 5/2007 | Gannoe et al. | |
| 7,220,266 B2 | 5/2007 | Gambale | |
| 7,229,428 B2 | 6/2007 | Gannoe et al. | |
| 7,232,445 B2 | 6/2007 | Kortenbach et al. | |

(Continued)

OTHER PUBLICATIONS

Cadiere, G.B., A. Rajan, M. Rqibate, O. Germay, G. Dapri, J. Himpens & A.K. Gawlicka. *Endoluminal Fundoplication (ELF)—Evolution of EsophyX™, A New Surgical Device for Transoral Surgery*. Minimally Invasive Therapy, 15:6, 2006, pp. 348-355.

(Continued)

*Primary Examiner* — Corrine M McDermott
*Assistant Examiner* — Gregory Anderson
(74) *Attorney, Agent, or Firm* — Douglas Denninger

(57) ABSTRACT

The present invention relates to devices and methods for the endoscopic treatment of hollow organs. The invention provides improved devices and methods for apposing and fixating multiple regions of the outer surface of a hollow organ. The invention is particularly useful for procedures in which multiple regions of the outer surface of the stomach are brought into apposition and fixated, for example procedures to treat gastroesophageal reflux disease (GERD) or procedures to treat obesity.

8 Claims, 35 Drawing Sheets

U.S. PATENT DOCUMENTS

| | | |
|---|---|---|
| 2001/0049497 A1 | 12/2001 | Kalloo et al. |
| 2002/0022851 A1 | 2/2002 | Kalloo et al. |
| 2006/0036164 A1 | 2/2006 | Wilson et al. |
| 2006/0135971 A1 | 6/2006 | Swanstrom et al. |
| 2006/0265042 A1* | 11/2006 | Catanese et al. ............. 623/1.11 |
| 2006/0282087 A1 | 12/2006 | Binmoeller |
| 2007/0135825 A1 | 6/2007 | Binmoeller |

OTHER PUBLICATIONS

Sclabas, Guido M., MD, Paul Swain, MD, and Lee L. Swanstrom, MD. *Endoluminal Methods for Gastrotomy Closure in Natural Orifice TransEnteric Surgery* (*Notes*). Surgical Innovation, vol. 13, No. 1, Mar. 2006, pp. 23-30.

* cited by examiner

METHODS AND DEVICES FOR ENDOSCOPIC TREATMENT OF ORGANS

CROSS-REFERENCE TO RELATED APPLICATION

This application claims priority to provisional patent application No. 60/891,057, filed 22 Feb. 2007.

FIELD OF THE INVENTION

The present invention relates to devices and methods for the endoscopic treatment of hollow organs.

BACKGROUND OF THE INVENTION

The present invention enables the endoscopic treatment of organs. It can be used to manipulate the wall of a hollow organ, and to fixate two or more regions of the wall of the hollow organ to each other. An example of a hollow organ for which this invention applies is the stomach. This invention is applicable to any procedure in which regions of the stomach are manipulated and affixed to one another. This invention is particularly useful for procedures in which multiple regions of the outer surface of the stomach are brought into apposition and fixated. Numerous procedures are enabled by this invention, for example procedures to treat gastroesophageal reflux disease (GERD) or procedures to treat obesity. A specific example of a GERD procedure which is enabled by this invention is plication of the stomach wall. Specific examples of obesity procedures which are enabled by this invention include stomach bypass or Roux-en-Y procedures, and stomach volume reduction procedures. The use of this invention to treat GERD will be used as an illustrative example.

The historical progression of the refinement of GERD treatment has been towards less invasive procedures. Open surgery, such as Nissen Fundoplication, was the treatment of choice for many years. Open surgery provides the advantages of allowing large areas of stomach tissue to be easily manipulated, providing access to the external wall of the stomach (serosa), and providing direct manipulation of tissues with the surgeon's hands and instruments. Disadvantages of open surgery include the risks associated with general anesthesia, the time required to gain access to the operative site, blood loss, the time required to close the tissues which were cut or dissected to obtain access to the operative site, post-operative pain, post-operative infection, lengthy post-operative recovery period, post-surgical adhesions, and cosmetic scarring due to large abdominal incisions. Additionally, risks of blood clots, pulmonary embolus, dehiscence, and pain are associated with open surgery.

Laparoscopic surgery, such as laparoscopic Nissen fundoplication, was next developed and popularized. Laparoscopic surgery provides the advantages of excellent, close-up visualization of tissues, fewer and smaller post-operative adhesions as compared to open surgery, and smaller cosmetic scarring. Laparoscopic surgery has the disadvantages of requiring a high degree of skill and training by the surgeon, and requiring specialized and expensive equipment.

Endoscopic procedures for the treatment of GERD were then developed. Examples of endoscopic GERD treatments can be seen in U.S. Pat. No. 6,663,639, Laufer, et al; U.S. Pat. No. 5,792,153 Swain et al. U.S. Pat. No. 6,254,598 Edwards, et al. U.S. Pat. No. 6,113,609 Adams; and U.S. Pat. No. 6,238,335 Silverman, et al. as well as a published article on Endogastric Solutions, *Minimally Invasive Therapy,* 2006, 15:6; 348-355. Endoscopic GERD treatments provide the advantages of less post-procedure pain and faster post-procedure recovery as compared to either open or laparoscopic surgical procedures, fewer post-procedure adhesions, no external scarring and the possibility of performing the procedure with the patient under sedation rather than general anesthesia. Disadvantages of endoscopic GERD treatment include lower efficacy as compared to open or laparoscopic surgical procedures, safety concerns during the procedures, and the complexity of the devices that are required to manipulate the tissue endoscopically.

Endoscopic procedures for the treatment of GERD can be separated into three categories. This first is procedures that modify tissue (e.g. U.S. Pat. No. 6,254,598 Edwards, et al). These procedures modify the tissue by applying energy, for example radiofrequency energy. Safety concerns with these procedures have led to discontinuation of their use in treating GERD.

The second category of endoscopic GERD treatment procedures is procedures that reshape tissue by adding foreign material (e.g. U.S. Pat. No. 6,238,335 Silverman, et al). These procedures introduce a foreign material, such as a polymer or collagen, into the tissue. A significant disadvantage of these procedures is that the physician cannot visualize the material as it is being implanted, and thus is not sure where in the body it is ending up. For example, the material may inadvertently be injected into the lumen of the aorta, which can result in death. The material may also migrate after implantation. These concerns have led to discontinuation of these procedures for the treatment of GERD.

The third category of endoscopic GERD treatment procedures is procedures that manipulate tissue to bring multiple regions of tissue together and fixate the tissue. These procedures are of two types. The first type of procedure that manipulates tissue to bring multiple regions of tissue together and fixate the tissue are procedures in which multiple regions of the inner surface of the stomach are brought into apposition and fixated. The device presented in (U.S. Pat. No. 5,792,153 Swain et al) has been used for this type of procedure. The stomach is lined with mucosal tissue, which has a low likelihood of healing to itself. Thus a disadvantage of this type of procedure is that often the tissue does not heal (i.e. mucosal-to-mucosal tissue apposition often does not heal). When the tissue does not heal it is less likely to remain in apposition over time, and thus the treatment is temporary and is not effective in treating GERD. The second type of procedure that manipulates tissue to bring multiple regions of tissue together and fixate the tissue are procedures in which multiple regions of the outer surface of the stomach are brought into apposition and fixated. The devices presented in (U.S. Pat. No. 6,663,639, Laufer, et al) and (*Minimally Invasive Therapy,* 2006, 15:6; 348-355) have been used for this type of procedure. The outer surface of the stomach is serosal tissue, which does tend to heal to itself (i.e. serosal-to-serosal apposition does tend to heal). Thus an advantage of this type of procedure is that the multiple regions of the outer surface of the stomach that are brought into apposition will heal to one another, and the treatment is permanent and thus is effective in treating GERD for a long period of time.

Thus to date the procedures in which multiple regions of the outer surface of the stomach are brought into apposition and fixated have been the most effective endoscopic treatments for GERD. The devices which currently exist for use in procedures in which multiple regions of the outer surface of the stomach are brought into apposition and fixated present several disadvantages, however.

The first disadvantage of the devices which currently exist for use in procedures in which multiple regions of the outer surface of the stomach are brought into apposition and fixated is that the devices must apply high loads in order to bring the regions of tissue into apposition. This is because the devices must apply the loads in a direction that is at an angle from the central axis of the shaft of the device. This geometry dictates that the devices have complex mechanisms, usually with hinged components. High loads must be applied near the base of the hinged components to obtain enough load at the distal end of the hinged components to manipulate the tissue sufficiently to bring multiple regions into apposition. Thus the mechanisms that actuate the hinged components are complex, expensive, and potentially unreliable.

The second disadvantage of the devices which currently exist for use in procedures in which multiple regions of the outer surface of the stomach are brought into apposition and fixated is that the complexity and expense of the devices dictates that the only practical way to enable them is as reusable devices. Reusable devices such as these must be cleaned and disinfected in between uses, and present the risk of cross-contamination from one patient to another. Disinfection also requires that the devices be sealed to prevent cleaning and disinfecting solutions from damaging the complex mechanisms, further increasing the cost of the devices and decreasing their reliability.

The third disadvantage of the devices which currently exist for use in procedures in which multiple regions of the outer surface of the stomach are brought into apposition and fixated is that the devices are large. This is due to the space required for the mechanisms discussed above. The large size of the devices, particularly the large cross-sectional areas, makes advancement through the esophagus difficult, which can increase patient discomfort, cause esophageal trauma or perforation and/or cause respiratory problems.

The fourth disadvantage of the devices which currently exist for use in procedures in which multiple regions of the outer surface of the stomach are brought into apposition and fixated is that device malfunction may require surgical intervention to allow removal of the device from the patient. If the actuating mechanism malfunctions when the device is engaged with the tissue, the device can become locked onto the stomach with no way to remove it endoscopically. In such an instance emergency surgical intervention is required to disengage the device from the tissue and remove the device from the patient. This puts the patient at risk for any of the complications normally associated with surgery, such as infection, pain, post-surgical adhesions, scarring, general anesthesia risk, and other generally known risks.

The fifth disadvantage of the devices which currently exist for use in procedures in which multiple regions of the outer surface of the stomach are brought into apposition and fixated is that the geometry of engaged regions of the stomach is limited, both in terms of location in the stomach, and in distance from each other, by the device geometry. Regions of the tissue that are brought together can only be regions that can be accessed by the portions of the device that engage tissue. The further apart from each other these regions are, the greater the mechanical challenge that the device must overcome in order to bring the regions into apposition.

The sixth disadvantage of the devices which currently exist for use in procedures in which multiple regions of the outer surface of the stomach are brought into apposition and fixated is that there is no way to ensure that structures outside of the stomach are not involved in the fixated tissue.

Thus, the ideal endoscopic procedure for the treatment of GERD will combine the advantages of open, laparoscopic and endoscopic treatments, without any of the disadvantages of these treatments. Specifically, the ideal endoscopic procedure for the treatment of GERD will:

allow large areas of stomach tissue to be easily manipulated;
allow access to the external wall of the stomach (serosa);
result in no cosmetic scarring;
minimize post-operative adhesions;
minimize post-procedure pain;
enable fast post-procedure recovery;
allow the possibility of performing the procedure with the patient under sedation rather than general anesthesia;
bring multiple regions of the outer surface of the stomach into apposition;
provide a high degree of efficacy;
not require loads to be applied at an angle from the central axis of the device;
utilize an apparatus which does not lock onto the tissue at any point during the procedure;
not require surgical intervention in the event of a device malfunction;
be possible with simple, inexpensive, disposable equipment;
be possible with devices that do not require hinged components;
be possible with devices that have a high degree of reliability;
be possible with devices that have a small cross-sectional area;
not limit the location of the points of engagement with the tissue;
allow points of tissue that are far from each other to be engaged and brought into apposition; and
ensure that structures outside of the stomach are not involved in the tissue engagement or fixation.

The invention presented herein satisfies these goals, and enables a new, novel, simple, safe and effective method for treating GERD. This invention may also treat other conditions in the stomach or elsewhere in the digestive tract, such as the small or large intestines, or the gall bladder. This invention may also be used to engage and fixation regions of multiple organs to each other, such as the small intestine to the stomach, for example. This invention may also have application in other hollow organs, such as for example the urinary bladder, heart or lungs.

BRIEF SUMMARY OF THE INVENTION

It is therefore an object of this invention to provide improved devices and methods for apposing and fixating multiple regions of the outer surface of a hollow organ.

It is a further object of this invention to provide improved devices and methods for apposing and fixating multiple regions of the outer surface of a hollow organ which allow large areas of tissue to be easily manipulated.

It is a further object of this invention to provide improved devices and methods for apposing and fixating multiple regions of the outer surface of a hollow organ which allow access to the external wall of the hollow organ.

It is a further object of this invention to provide improved devices and methods for apposing and fixating multiple regions of the outer surface of a hollow organ which result in no cosmetic scarring.

It is a further object of this invention to provide improved devices and methods for apposing and fixating multiple regions of the outer surface of a hollow organ which minimize post-operative adhesions.

It is a further object of this invention to provide improved devices and methods for apposing and fixating multiple regions of the outer surface of a hollow organ which minimize post-procedure pain.

It is a further object of this invention to provide improved devices and methods for apposing and fixating multiple regions of the outer surface of a hollow organ which enable fast post-procedure recovery.

It is a further object of this invention to provide improved devices and methods for apposing and fixating multiple regions of the outer surface of a hollow organ which allow the possibility of performing the procedure with the patient under sedation rather than general anesthesia.

It is a further object of this invention to provide improved devices and methods for apposing and fixating multiple regions of the outer surface of a hollow organ which provide a high degree of efficacy for the condition being treated.

It is a further object of this invention to provide improved devices and methods for apposing and fixating multiple regions of the outer surface of a hollow organ which do not require loads to be applied at an angle from the central axis of the device.

It is a further object of this invention to provide improved devices and methods for apposing and fixating multiple regions of the outer surface of a hollow organ which utilize an apparatus which does not lock onto the tissue at any point during the procedure;

It is a further object of this invention to provide improved devices and methods for apposing and fixating multiple regions of the outer surface of a hollow organ which do not require surgical intervention in the event of a device malfunction.

It is a further object of this invention to provide improved devices for apposing and fixating multiple regions of the outer surface of a hollow organ which are simple, inexpensive and disposable.

It is a further object of this invention to provide improved devices and methods for apposing and fixating multiple regions of the outer surface of a hollow organ which do not require hinged components.

It is a further object of this invention to provide improved devices and methods for apposing and fixating multiple regions of the outer surface of a hollow organ which perform with a high degree of reliability.

It is a further object of this invention to provide improved devices for apposing and fixating multiple regions of the outer surface of a hollow organ which be have a small cross-sectional area.

It is a further object of this invention to provide improved devices and methods for apposing and fixating multiple regions of the outer surface of a hollow organ which do not limit the location of the points of engagement with the tissue.

It is a further object of this invention to provide improved devices and methods for apposing and fixating multiple regions of the outer surface of a hollow organ which allow points of tissue that are far from each other to be engaged and brought into apposition.

It is a further object of this invention to provide improved devices and methods for apposing and fixating multiple regions of the outer surface of a hollow organ which ensure that structures outside of the stomach are not involved in the tissue engagement or fixation.

The invention presented herein accomplishes all of these objects in a way that is not possible with prior art devices and methods. The invention includes a novel system incorporating an instrument, an inner tube, a piercing element, a first tissue anchor, a pusher, a suture and a second tissue anchor.

The method for apposing and fixating multiple regions of the outer surface of a hollow organ is performed by advancing various elements of the system through the working channel of a flexible endoscope. The piercing element is advanced through the wall of the organ to create a hole at a first location. A location indicator and an optical receiver are provided to allow the location of the distal end of the instrument shaft to be determined from within the organ. The wall of the organ is then pierced at a second location. The first tissue anchor and suture are delivered through the first and second holes in the wall of the organ. The second tissue anchor is advanced along the suture, thus bringing the first and second tissue anchors closer to one another, and apposing and fixating multiple regions of the outer surface of the organ.

This invention features a system for creating and fixating a fold in the wall of a hollow organ by bringing multiple regions of the outer surface of the organ into apposition. This system includes a first tube having a lumen, a proximal end and a distal end positionable within the organ. This system also includes a second tube having a lumen, a proximal end and a distal end, the second tube configured to pass through the lumen of the first tube into the organ. This system also includes a piercing element configured to pass through the lumen of the second tube to pierce the organ, position the distal end of the second tube outside of the organ, again pierce the organ, and position the distal end of the second tube back inside the organ. This system also includes a first tissue anchor having a first state configured to pass through the lumen of the second tube and a second state configured for tissue fixation. This system also includes a suture attached to the first tissue anchor. This system also includes a second tissue anchor having a first state configured to pass through the lumen of the first tube and slideably engaged with the suture, and a second state configured to fixate tissue and lock onto the suture. This system also includes a location indicator associated with the distal end of the second tube. This system also includes an optical receiver associated with the distal end of the first tube for identifying the location of the distal end of the second tube when it is outside the organ.

In another aspect the invention includes a system for apposing and fixating tissue. This system includes a tube having a lumen, a proximal end and a distal end. This system also includes a piercing element configured to pass through the lumen of the tube. This system also includes a first tissue anchor having a first state configured to pass through the lumen of the tube and a second state configured for tissue fixation. This system also includes a suture attached to the first tissue anchor. This system also includes a second tissue anchor having a first state configured to pass through the lumen of a tube and slideably engaged with the suture, and a second state configured to fixate tissue and lock onto the suture.

In another aspect the invention includes a system for apposing and fixating tissue. This system includes a first tissue anchor having a first state configured to pass through a lumen of a tube and a second state configured to fixate tissue. This system also includes a suture attached to the first tissue anchor. This system also includes a second tissue anchor having a first state configured to pass through the lumen of a tube and slideably engaged with the suture, and a second state configured to fixate tissue and lock onto the suture.

Another aspect the invention is a method of creating and fixating a fold in the wall of a hollow organ. This method includes piercing the wall of a hollow organ at a first location from the inside of the organ to the outside of the organ to create a first hole in the wall of the organ. This method also includes advancing an elongated member through the first hole in the wall of the organ. This method also includes positioning the distal end of the elongated member near the outer wall of the organ at a second location. This method also includes detecting from within the organ the position of the distal end of the elongated member. This method also includes piercing the wall of the organ at the second location from the outside of the organ to the inside of the organ to create a second hole in the wall of the organ. This method also includes advancing the elongated member back into the organ through the second hole in the wall of the organ. This method also includes delivering a first tissue anchor and a suture through the first and second holes in the wall of the organ, the first tissue anchor being attached to the suture. This method also includes delivering a second tissue anchor over the suture and advancing the second tissue anchor over said suture, thereby moving the first and second holes in the wall of the organ towards one another and bringing multiple regions of the outer surface of the organ into apposition. This method also includes locking the second tissue anchor onto the suture.

Another aspect of the invention is a method of detecting the position of a medical device within the body. This method includes placing the medical device within the body and in proximity to tissue. This method also includes placing the distal end of an endoscope within the body on the opposite side of the tissue. This method also includes emitting light from the medical device. This method also includes viewing the tissue with the endoscope and observing the light shining through the tissue, thus detecting the position of the medical device.

DETAILED DESCRIPTION OF THE INVENTION

Figure 1:
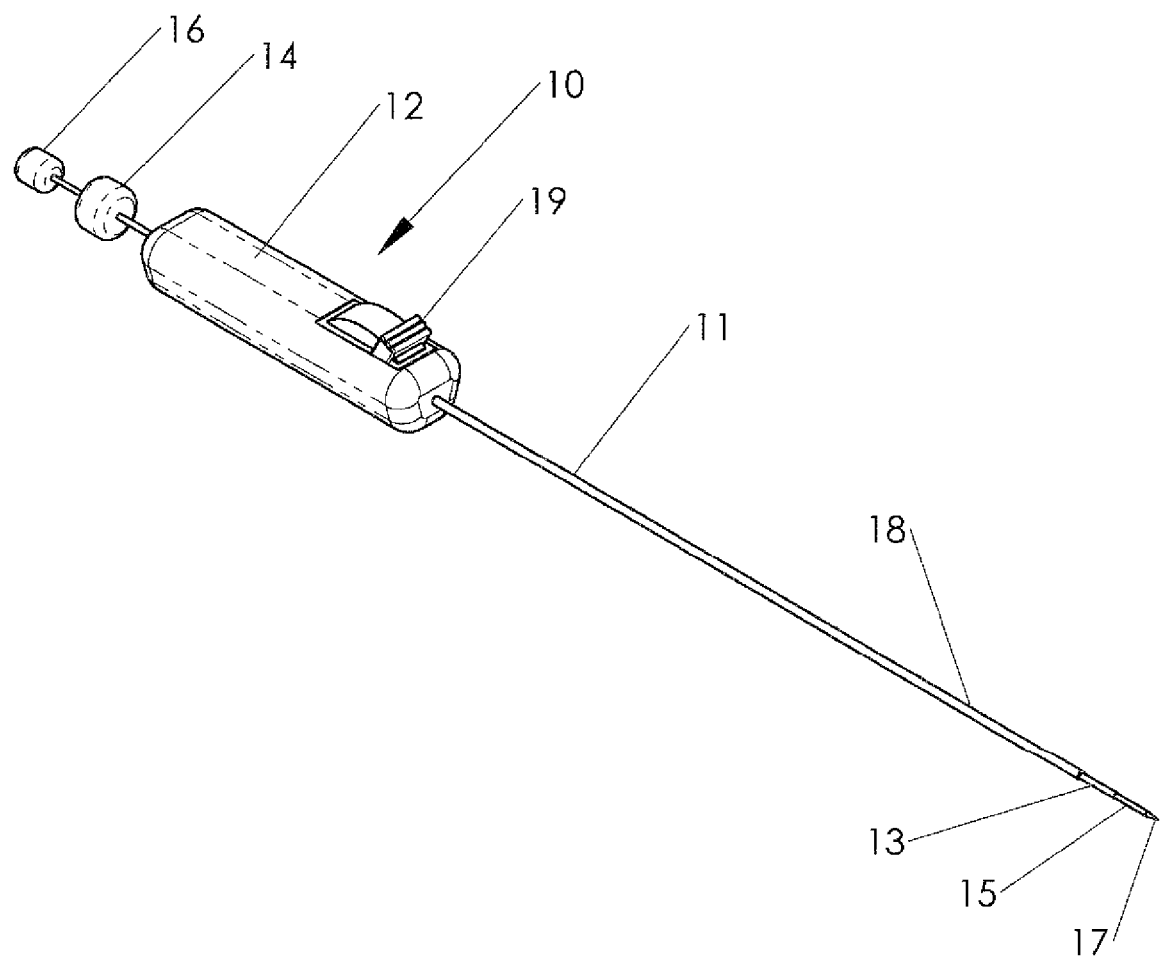
FIG. 1 is a perspective view of the portion of the invention that comprises an instrument, depicting the distal instrument shaft in the straight configuration.

The invention will now be described in detail, with references made to the accompanying drawings. Reference numbers are used in the drawings and the description to refer to specific elements or aspects of the invention. Wherever possible the same reference numbers will be used to indicate the same elements or aspects throughout multiple drawings and descriptions.

FIGS. 1-15 and 36-38 illustrate a preferred embodiment of the invention, and FIGS. 16-35 illustrate the novel method which is enabled by the invention. Alternate embodiments will be described in reference to each figure.

FIG. 1 shows an instrument 10 which is used to create and fixate a fold in the wall of a hollow organ. The instrument includes a shaft 11 which is tubular, with an internal lumen passing through the tube. Instrument shaft 11 is an elongated member with a proximal end and a distal end, and is sized to fit within the working channel of a flexible endoscope. In a preferred embodiment instrument shaft 11 has an outer diameter of 2.8 mm or less. In another embodiment instrument shaft has an outer diameter of approximately 2.7 mm, an inner diameter of approximately 2.1 mm and a length of approximately 1.5 meters. The length of instrument shaft 11 as depicted shortened in FIG. 1 to allow the entire instrument 10 to be depicted clearly in one figure. In a preferred embodiment instrument shaft 11 is constructed from polymer, such as Pebax, polyurethane, polyimide or other materials known to one skilled in the art. Instrument shaft 11 may also include a structure to provide torsional strength, such as a wire braid impregnated within the wall of instrument shaft 11. Instrument handle 12 is attached to the proximal end of instrument shaft 11. An inner tube 13 is an elongated member which passes through instrument handle 12 and the lumen of instrument shaft 11. Inner tube 13 is free to advance, retract and rotate relative to instrument shaft 11. In a preferred embodiment inner tube 13 has an outer diameter of approximately 2.0 mm, and an inner diameter of approximately 1.8 mm.

An inner tube handle 14 is attached to the proximal end of inner tube 13. Inner tube handle 14 provides a means for the operator to advance, retract and/or rotate inner tube 13. A piercing element 15 is an elongated member which passes through the lumen of inner tube 13. Piercing element 15 is free to advance, retract or rotate relative to inner tube 13. In a preferred embodiment piercing element 15 has an outer diameter of approximately 1.5 mm. A piercing element handle 16 is attached to the proximal end of piercing element 15. Piercing element handle 16 provides a means for the operator to advance, retract and/or rotate piercing element 15. The distal end 17 of piercing element 15 is configured to pierce tissue. In one embodiment distal end 17 of piercing element 15 is a sharpened point, such as a conical tip or a trocar tip. In another embodiment piercing element 15 is configured to deliver electrical current to tissue, enabling distal end 17 to cauterize the tissue when piercing. Instrument shaft 11 includes an articulating section 18 at its distal end. Instrument handle 12 includes an articulation control 19 which actuates articulating section 18. Articulation control 19 as shown is a lever which the operator can pull back or move forward. In another embodiment articulation control 19 is a knob which the operator turns. Articulation control 19 may be any other suitable control that is known in the art. When the operator actuates articulation control 19 articulating section 18 will articulate, or change shape from a straight to a bent configuration. The mechanism that causes articulating section 18 to articulate, as well as the connection between articulation control 19 and articulating section 18 are as is known in the art. In one embodiment a pullwire connects articulation control 19 and articulating section 18. The pullwire can be incorporated within the wall of instrument shaft 11, or the pullwire can be positioned outside the outer diameter of instrument shaft 11. In another embodiment articulating section 18 is pre-formed into a bent shape, and does not require the user to activate a mechanism to articulate articulating section 18. In this embodiment articulating section 18 is straightened when it is inserted through and endoscope working channel, and then it regains a pre-formed bent configuration when it extends beyond the distal end of the endoscope working channel, and is no longer constrained.

Figure 2:
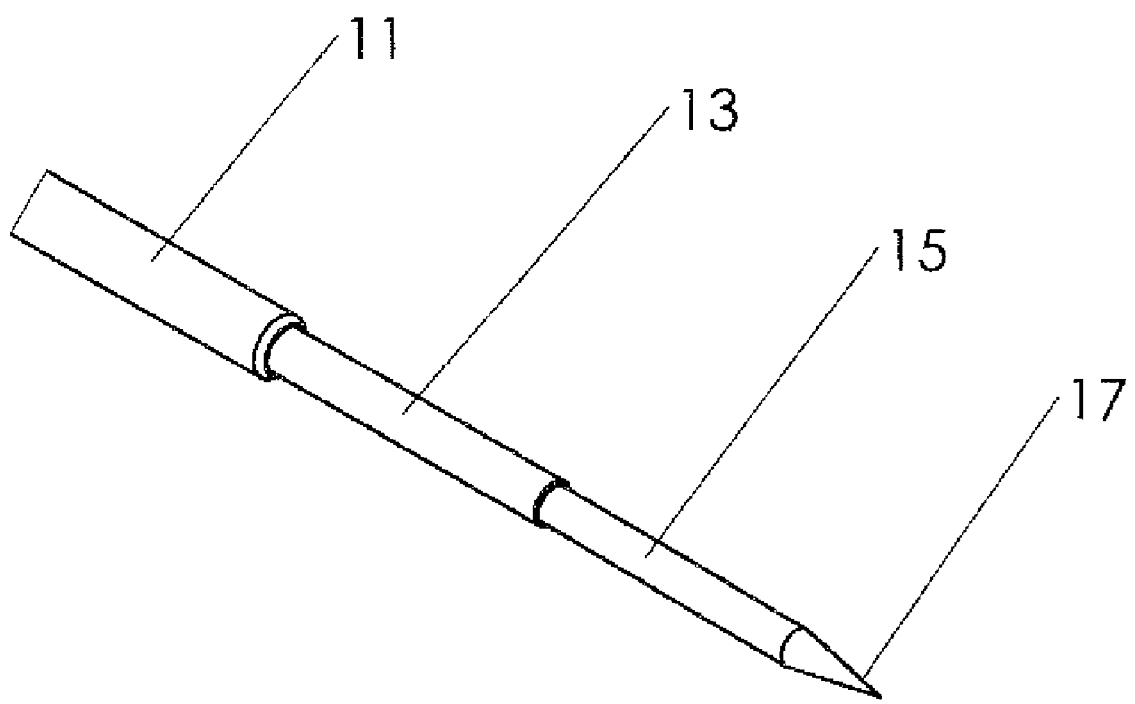
FIG. 2 is a detail perspective view of the distal portion of the instrument.

FIG. 2 is a detail view of the distal ends of instrument shaft 11, inner tube 13 and piercing element 15. This view illustrates piercing element 15 protruding from inner lumen of inner tube 13, and inner tube 13 protruding from the inner lumen of instrument shaft 11.

Figure 3:
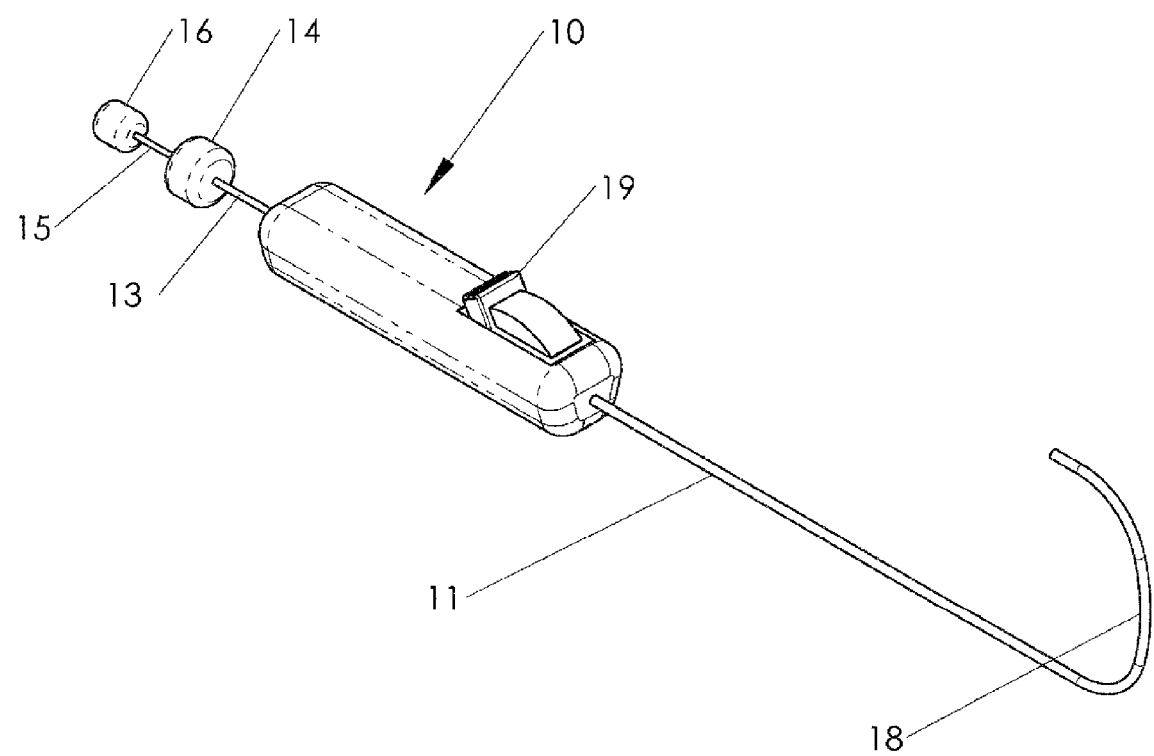
FIG. 3 is a perspective view of the instrument, depicting the distal instrument shaft in an articulated configuration.

FIG. 3 shows instrument 10 in an articulated configuration. The operator has pulled back articulation control 19, causing articulating section 18 to articulate. Inner tube 13 and piercing element 15 have been retracted by pulling inner tube handle 14 and piercing element handle 16 back, so that neither inner tube 13 nor piercing element 15 protrude from the distal end of instrument shaft 11.

Figure 4:
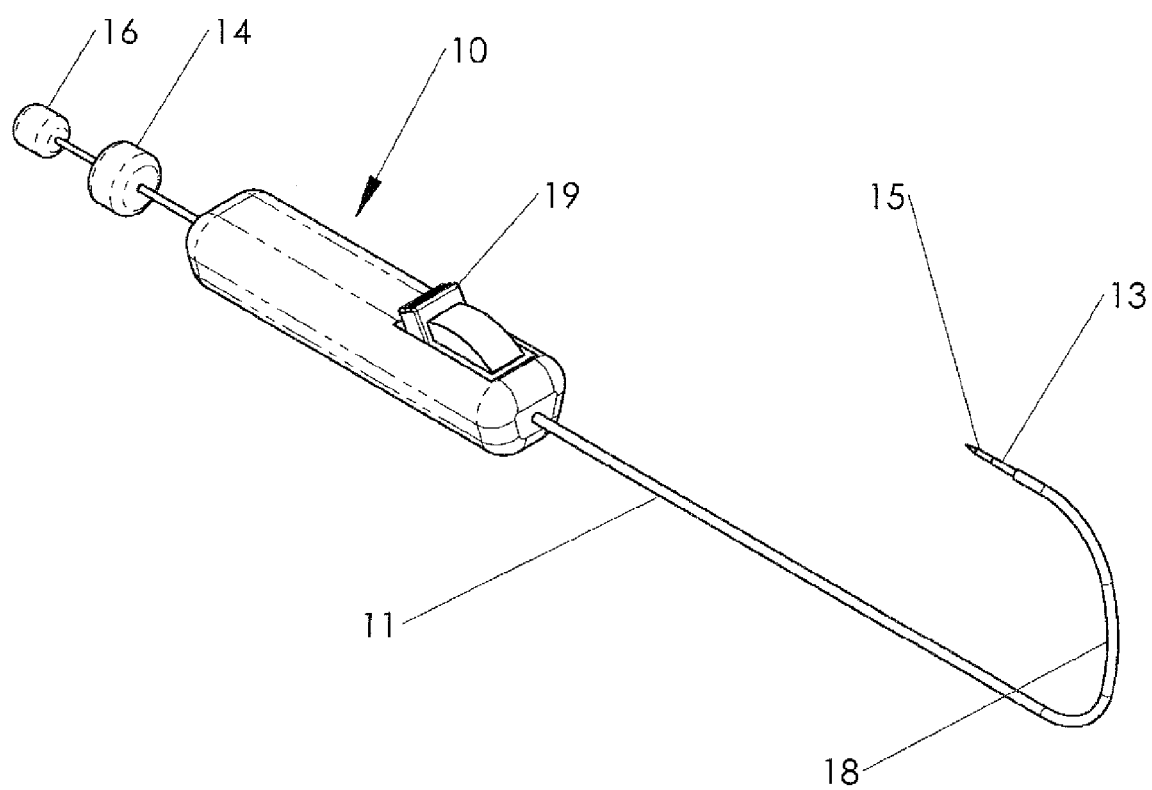
FIG. 4 is a perspective view of the instrument, depicting the distal instrument shaft in an articulated configuration and the distal end of a piercing element extended beyond the distal end of the instrument.

FIG. 4 shows articulated instrument 10 with both inner tube 13 and piercing element 15 advanced so that they protrude beyond the distal end of instrument shaft 11. The operator has advanced inner tube 13 and piercing element 15 by advancing inner tube handle 14 and piercing element handle 16.

Figure 5:
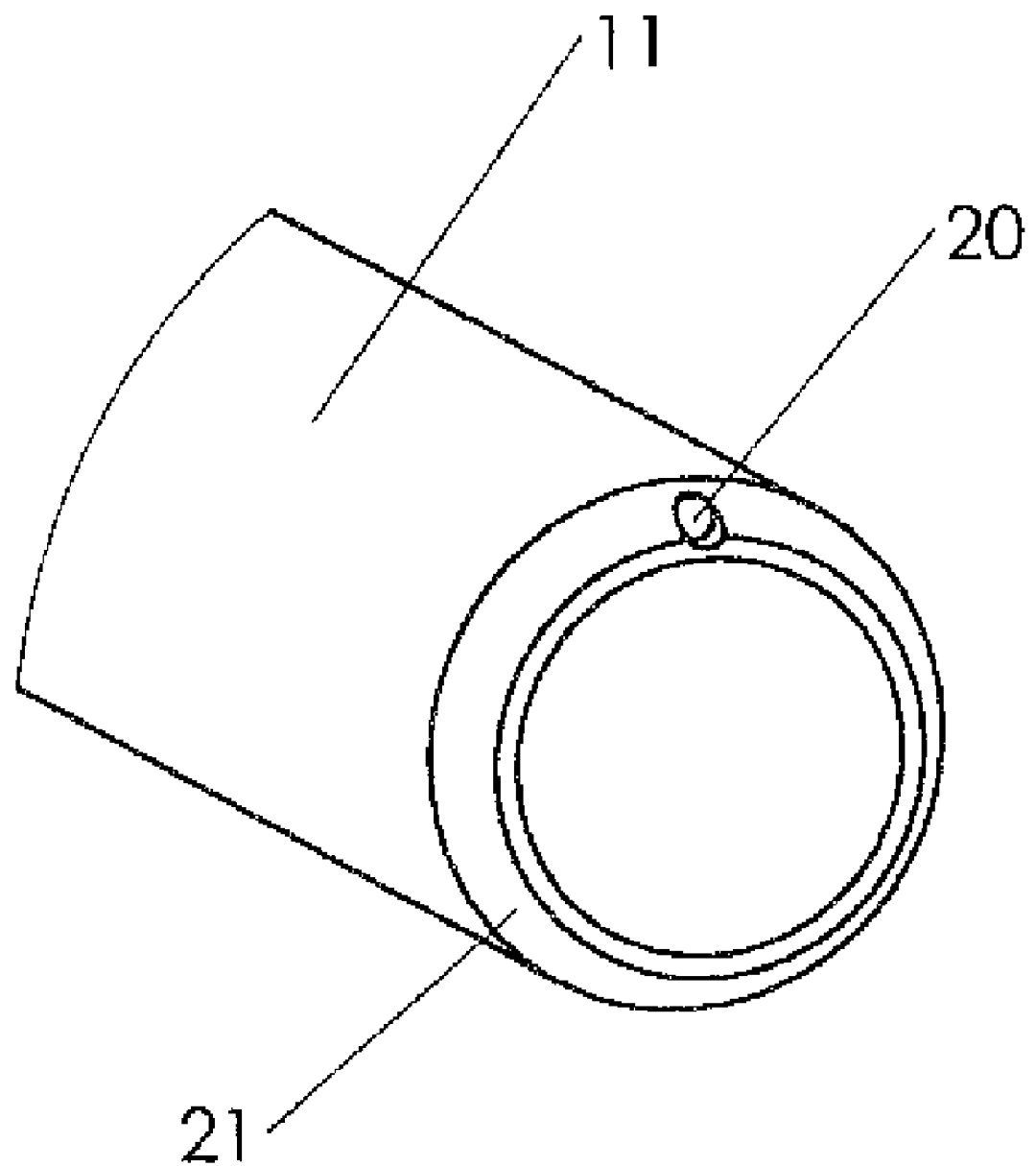
FIG. 5 is a detail perspective view of the distal end of the instrument shaft.

FIG. 5 is a detail view of the distal end of instrument shaft 11. Instrument 10 includes a light source which extends from instrument handle 12 and within the wall of instrument shaft 11, terminating at the distal end of instrument shaft 11. Distal end 20 of the light source is exposed, so that light that is transmitted to distal end 20 can shine beyond the distal end of instrument shaft 11. In a preferred embodiment the light source consists of a light generator, such as a light bulb or a laser, and a fiber optic bundle which is incorporated within the wall of instrument shaft 11. In another embodiment the light source consists of a light emitting diode at distal end 20 of the light source, and wires that are incorporated within the wall of instrument shaft 11 and connect to a power source. The power source may be a battery contained within instrument handle 12, or a power source that is external to instrument 10. In the embodiment in which the power source is external to instrument 10 an electrical cord extends from instrument handle 12 to connect to the external power source. One skilled in the art will be able to envision numerous ways to incorporate a light source which terminates at the distal end of instrument shaft 11.

FIG. 5 also shows a tapered section 21 at the distal end of instrument shaft 11. Tapered section 21 provides a gradual transition in outer diameter of instrument shaft 11. Tapered section 21 in a preferred embodiment is a chamfer. In another embodiment tapered section 21 is a radiused edge.

Figure 6:
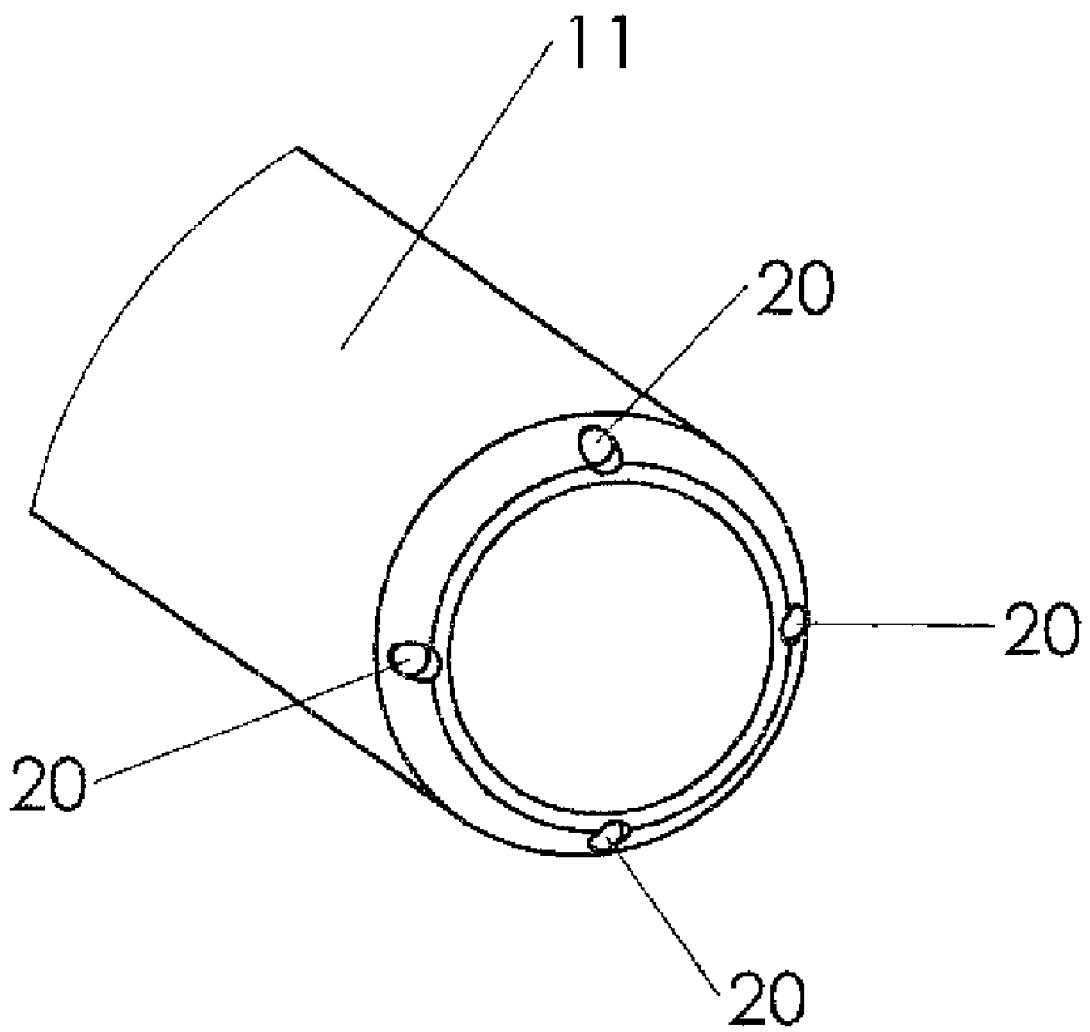
FIG. 6 is a detail perspective view of the distal end of an alternate configuration of the instrument shaft.

FIG. 6 shows an alternate embodiment of the distal end of instrument shaft 11. In this embodiment there are four locations where distal end 20 of the light source terminates, distributed around the distal end of instrument shaft 11. Alternate embodiments include two, three, or more than four locations where distal end 20 of the light source terminates. In another embodiment the light source is incorporated into inner tube 13 rather than instrument shaft 11. In another embodiment the light source is incorporated into piercing element 15 rather than instrument shaft 11. In another embodiment the light source is inserted through the lumen of instrument shaft 11 or the lumen of inner tube 13.

Figure 7:
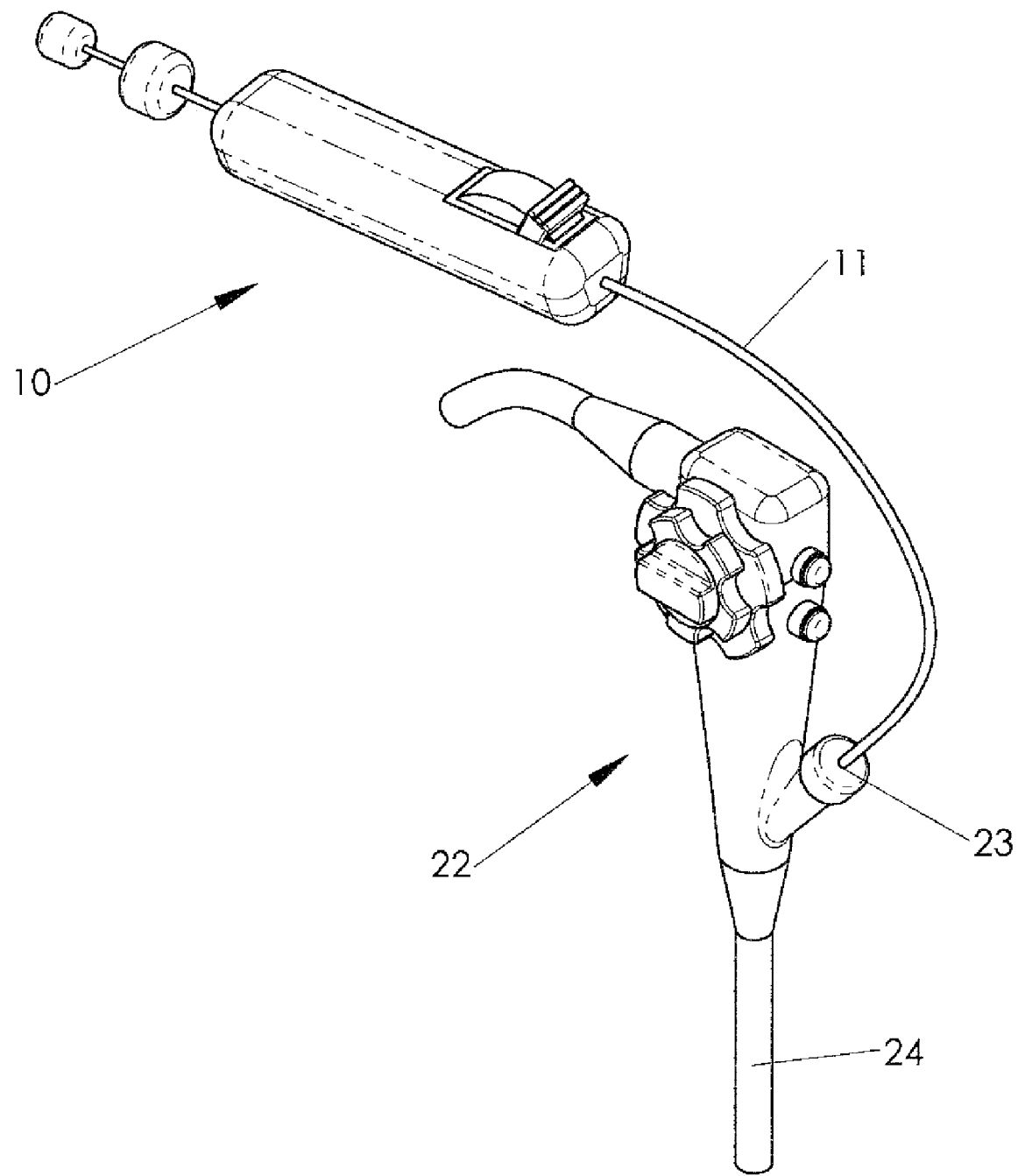
FIG. 7 is a perspective view depicting the shaft of the instrument inserted into the working channel of an endoscope.
Figure 8:
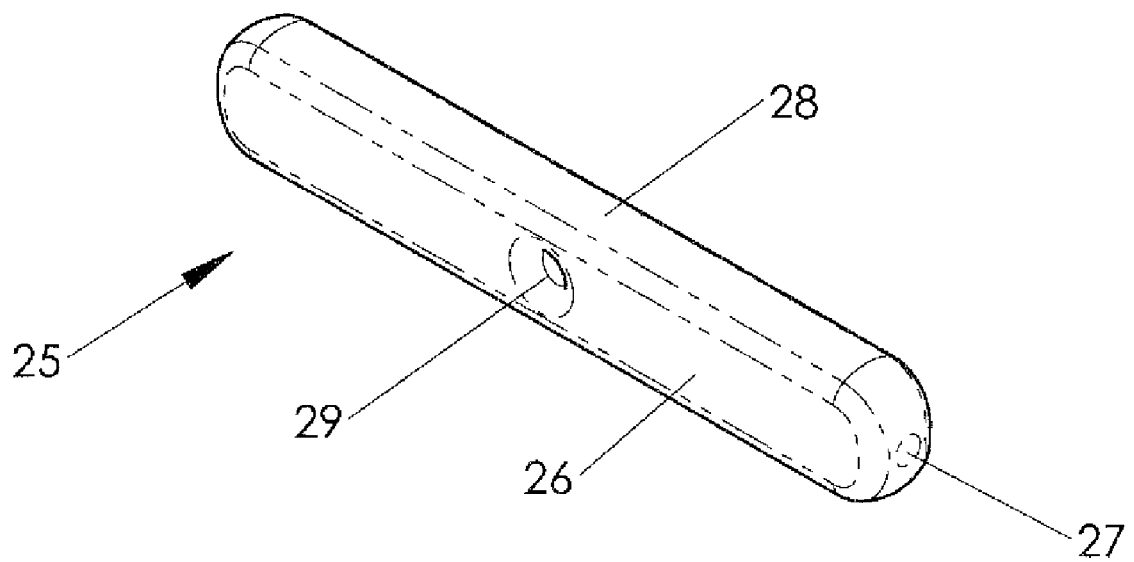
FIG. 8 is a perspective view of a first tissue anchor.

FIG. 7 shows instrument 10 with instrument shaft 11 inserted into working channel 23 of a flexible endoscope 22. The flexible endoscope shaft 24 is shown shortened in this figure. Instrument shaft 11 extends through endoscope working channel 23, allowing the operator to advance instrument 10 so that articulating section 18 protrudes beyond the distal end of flexible endoscope shaft 24.

Figure 9:
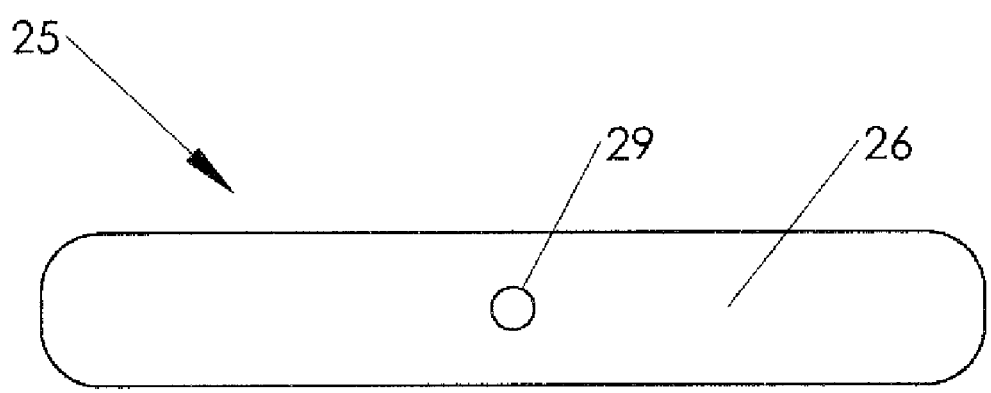
FIG. 9 is a view of the front of the first tissue anchor.
Figure 10:
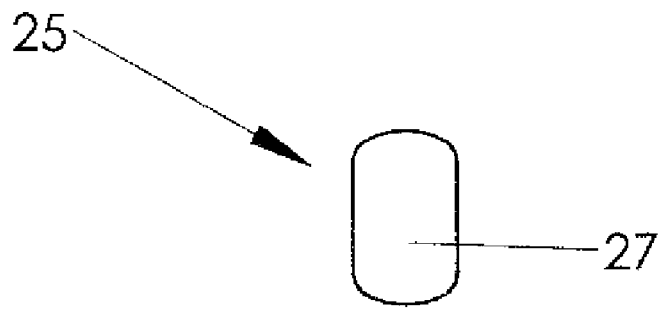
FIG. 10 is a view of the side of the first tissue anchor.
Figure 11:
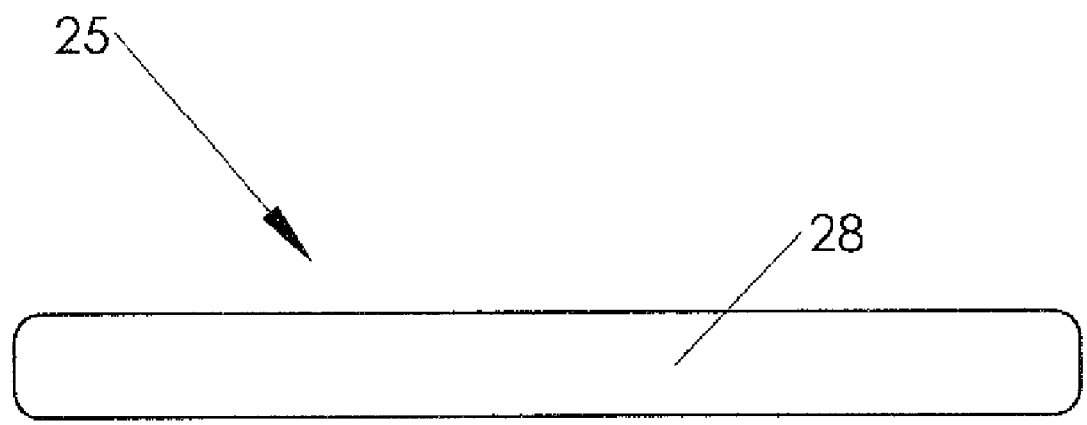
FIG. 11 is a view of top of the first tissue anchor.

FIGS. 8-11 show a first tissue anchor 25. First tissue anchor 25 consists of a bar of rigid, biocompatible material. In a preferred embodiment first tissue anchor 25 is constructed from titanium. In alternate embodiments first tissue anchor 25 is constructed from stainless steel, polyacetal, polypropylene, polyethylene, PEEK, polylactic acid, polyglycolic acid, or any other metal, non-absorbable plastic, bioabsorbable plastic or biocompatible ceramic material known in the art. First tissue anchor 25 includes a front face 26, a side face 27 and a top face 28. A hole 29 extends through the first tissue anchor 25 in a direction perpendicular to front face 26. FIG. 9 shows front face 26 of first tissue anchor 25. The rear face of first tissue anchor 25 is on the opposite side of the anchor from front face 26. Hole 29, which extends completely through first tissue anchor 25 is visible in FIG. 9. FIG. 10 shows side face 27 of first tissue anchor 25, and FIG. 11 shows top face 28 of first tissue anchor 25. The bottom face of first tissue anchor 25 is on the opposite side of the anchor from top face 28. In a preferred embodiment of the invention, hole 29 is circular in cross-section, and is sized to allow one length of suture to pass freely through hole 29. For example, hole 29 may have a cross-sectional diameter of 0.35-0.50 mm if first tissue anchor 25 is to be used with a U.S.P. size 2-0 suture, which has a cross-sectional diameter of approximately 0.30 mm. In another embodiment hole 29 is sized to allow multiple strands of suture to pass through hole 29. In a preferred embodiment the dimensions of first tissue anchor 25 are approximately 10 mm across the width of front face 26, approximately 1.50 mm height of side face 27, and approximately 0.80 mm height of top face 28, i.e. a distance of approximately 0.80 mm from the front face 26 to the back face.

Figure 12:
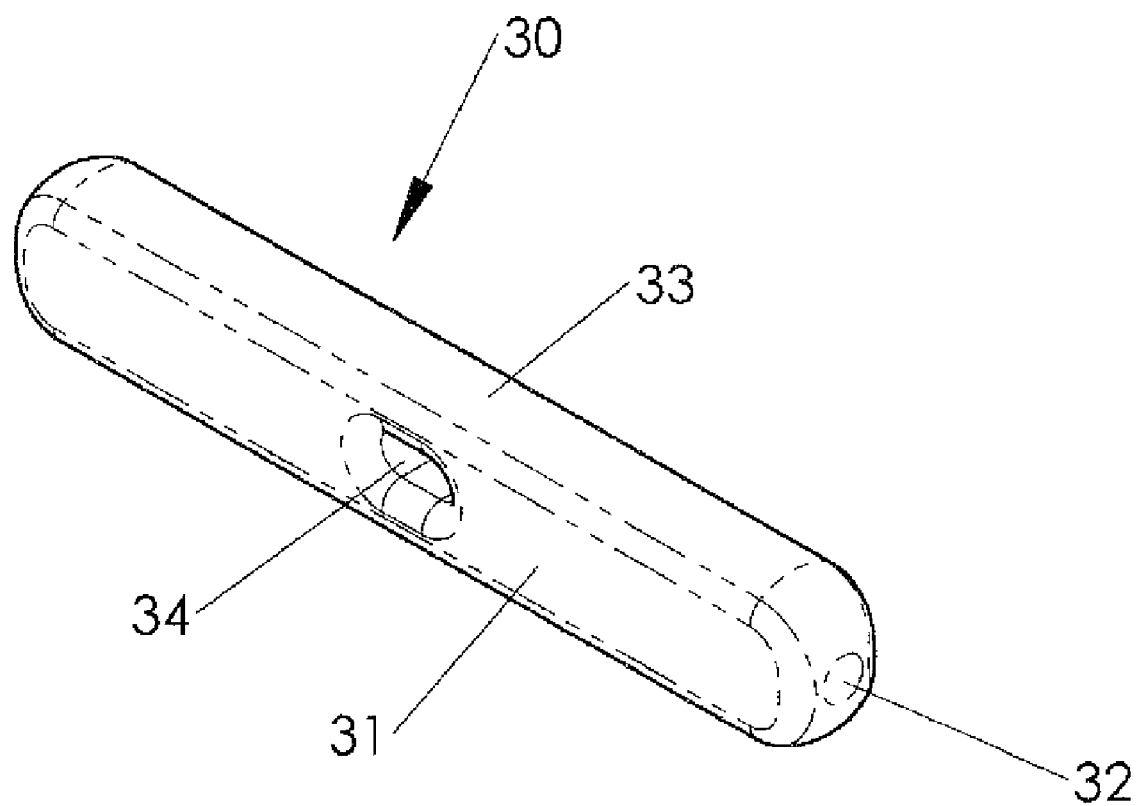
FIG. 12 is a perspective view of a second tissue anchor.

FIG. 12 shows a second tissue anchor component 30. Second tissue anchor component 30 consists of a bar of rigid, biocompatible material. In a preferred embodiment second tissue anchor component 30 is constructed from titanium. In alternate embodiments second tissue anchor component 30 is constructed from stainless steel, polyacetal, polypropylene, polyethylene, PEEK, polylactic acid, polyglycolic acid, or any other metal, non-absorbable plastic, bioabsorbable plastic or biocompatible ceramic material known in the art. Second tissue anchor component 30 includes a front face 31, a side face 32 and a top face 33. Opposite front face 31 is a rear face, and opposite top face 33 is a bottom face. A hole 34 extends through second tissue anchor component 30 in a direction perpendicular to front face 31. Hole 34 is sized to allow two lengths of suture to pass freely through hole 34. Hole 34 may have an oval cross-sectional shape in order to allow multiple lengths of suture to pass freely through hole 34. For example, the dimensions of the oval cross-section of hole 34 may be 0.40 mm by 0.80 mm if second tissue anchor component 30 is to be used with a U.S.P. size 2-0 suture, which has a cross-sectional diameter of approximately 0.30 mm.

Figure 13:
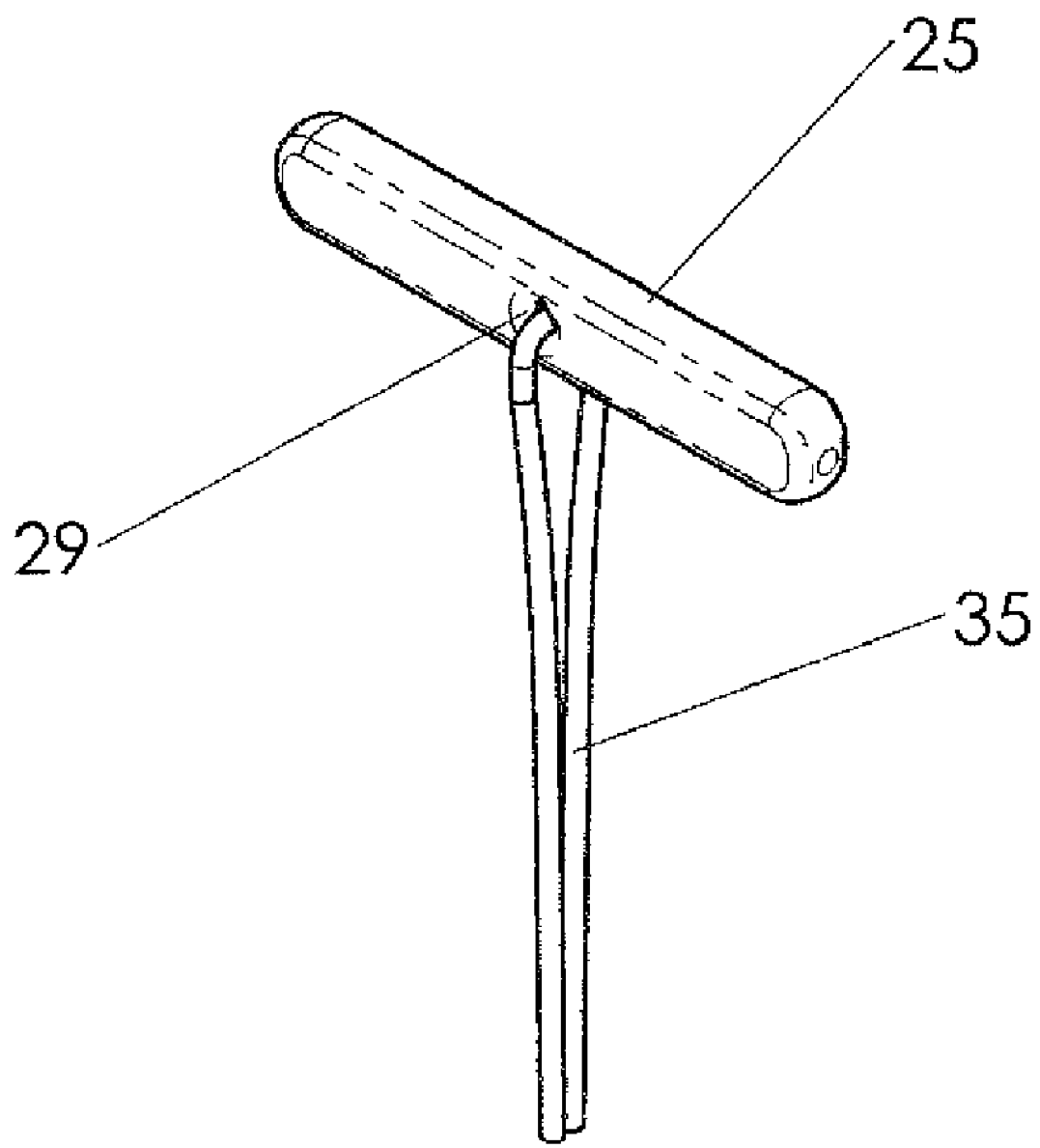
FIG. 13 is a perspective view of the first tissue anchor combined with a suture.

FIG. 13 shows first tissue anchor 25 with a suture 35 passing through hole 29. First tissue anchor 25 is free to rotate relative to suture 35. In FIG. 13 first tissue anchor is configured for tissue fixation. As used herein "configured for tissue fixation" means that a relatively large surface area of the tissue anchor is presented in an orientation that will interact with the tissue. When suture 35 is configured for tissue fixation, the bottom face of first tissue anchor 25 will interact with the tissue. In a preferred embodiment the surface area of the bottom face of first tissue anchor 25 is equal to the width of the bottom face times the height of the bottom face, or approximately 10.00 mm times 0.80 mm, which equals 8.00 mm$^2$. This is substantially greater than the cross-sectional area of the lumen of the inner tube, which in a preferred embodiment equals approximately 2.75 mm.

Figure 14:
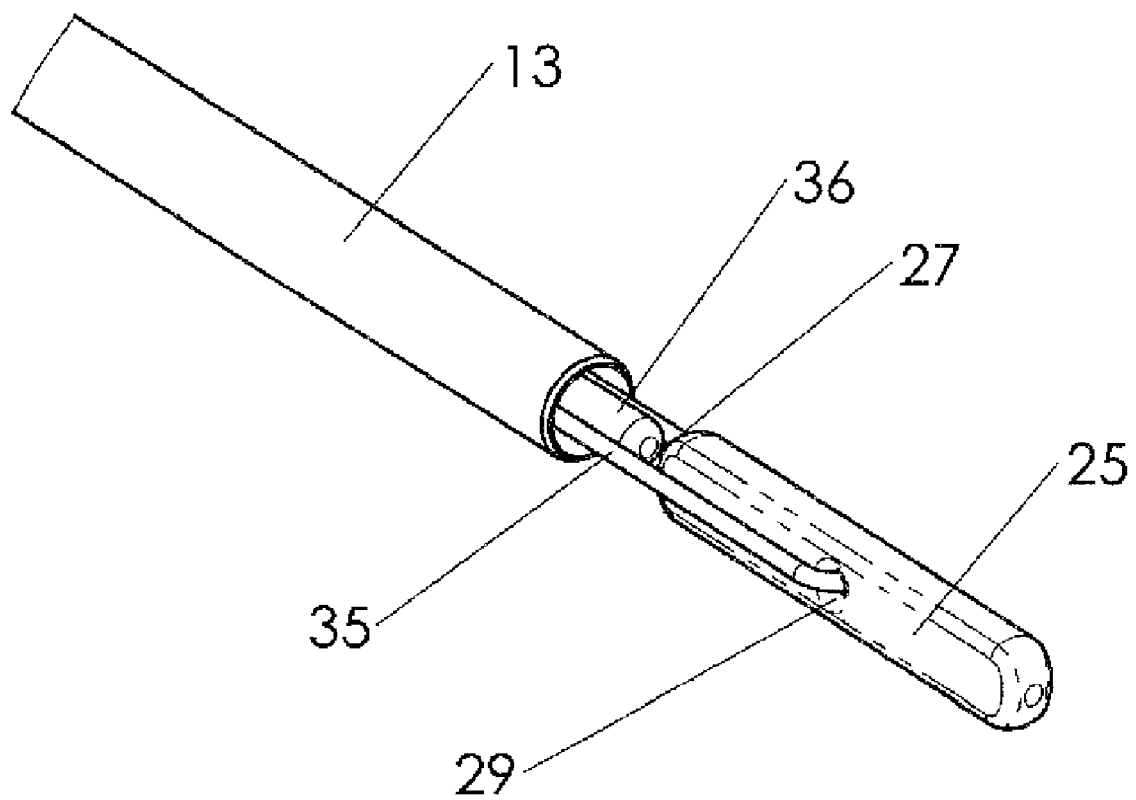
FIG. 14 is a perspective view of the first suture anchor combined with a suture and the distal end of a tube, where the anchor and suture are protruding from the lumen of the tube.

FIG. 14 shows first suture anchor 25 with suture 35 through hole 29. In FIG. 14 first tissue anchor 25 is configured to pass through the lumen of inner tube 13. In this configuration first tissue anchor 25 is rotated 90 degrees relative to suture 35 as compared to the configuration shown in FIG. 13. The distal end of pusher 36 is shown protruding from the lumen of inner tube 13. Pusher 36 passes through inner tube 13 and is used to advance first tissue anchor 25 through the lumen of inner tube 13, to deliver first tissue anchor to a treatment site within the body. Pusher 36 has sufficient compressive strength to allow it to advance first tissue anchor 25 through the lumen of inner tube 13. Pusher 36 also has sufficient flexibility to allow it to advance through the lumen of inner tube 13 when inner tube 13 is bent by endoscope shaft 24 and/or articulating section 18 or instrument shaft 11. Pusher 36 may be constructed from metal or plastic, and may be solid or tubular. In another embodiment pusher 36 is constructed as a wire coil.

Figure 15:
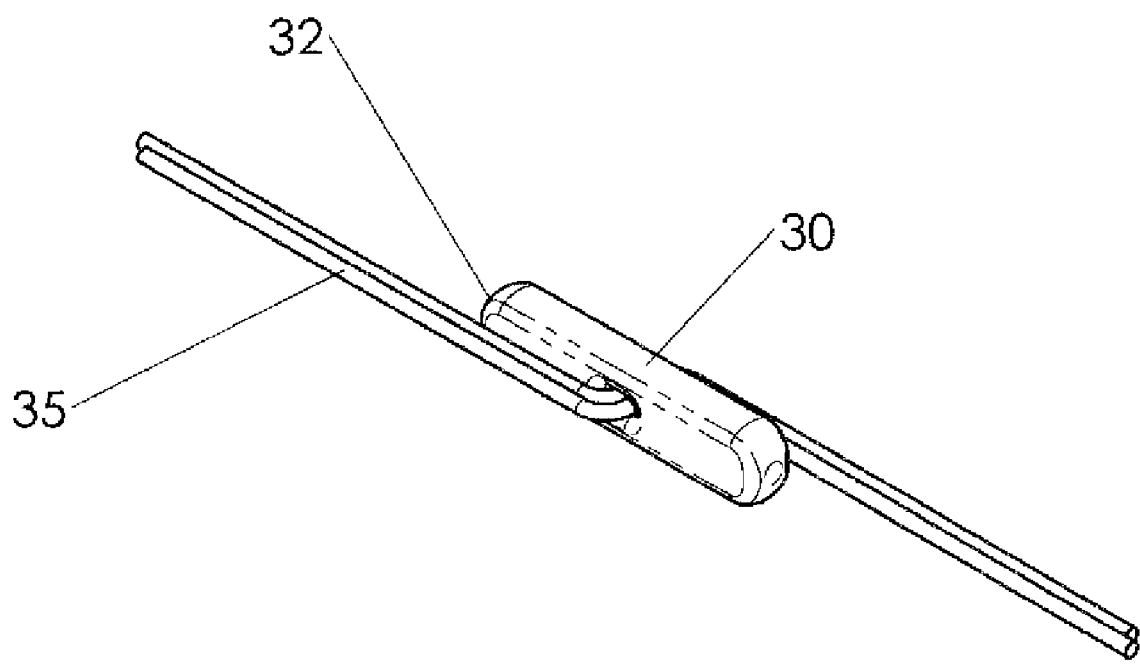
FIG. 15 is a perspective view of the second suture anchor combined with two lengths of suture.

FIG. 15 shows second tissue anchor component 30 with suture 35 through hole 34. In FIG. 15 second tissue anchor component 30 is configured to pass through the lumen of a tube, such as working channel 23 of flexible endoscope 22. Second tissue anchor component 30 can be advanced over suture 35 and through working channel 23 of flexible endoscope 22 by pushing side face 32.

Other tissue anchors which are known in the art may also be used as part of this invention. Examples of other tissue anchors know in the art include T-bars, elastomeric disks, cones, cups or hemispheres, umbrella-like structures, self-expanding wire structures, expandable foam structures, inflatable structures, or any anchor structure known in the art. Multiple T-bars or other combinations of anchors may be used to increase the surface area with which the tissue anchor engages the tissue. Multiple T-bars may align in series within the lumen through which they are delivered, but then form a crossed configuration upon deployment through and against the tissue.

The novel method which is enabled by the invention will now be illustrated with reference to FIGS. 16-35. The invention makes possible a new and novel method of creating and fixating a fold in a hollow organ in which multiple regions of the outer surface of the hollow organ are brought into apposition and fixated. Numerous procedures are enabled by this invention, for example procedures to treat gastroesophageal reflux disease (GERD) or procedures to treat obesity. A specific example of a GERD procedure which is enabled by this invention is plication of the stomach wall. Specific examples of obesity procedures which are enabled by this invention include stomach bypass or Roux-en-Y procedures, and stomach volume reduction procedures. The use of this invention to treat GERD will be used as an illustrative example.

Figure 16:
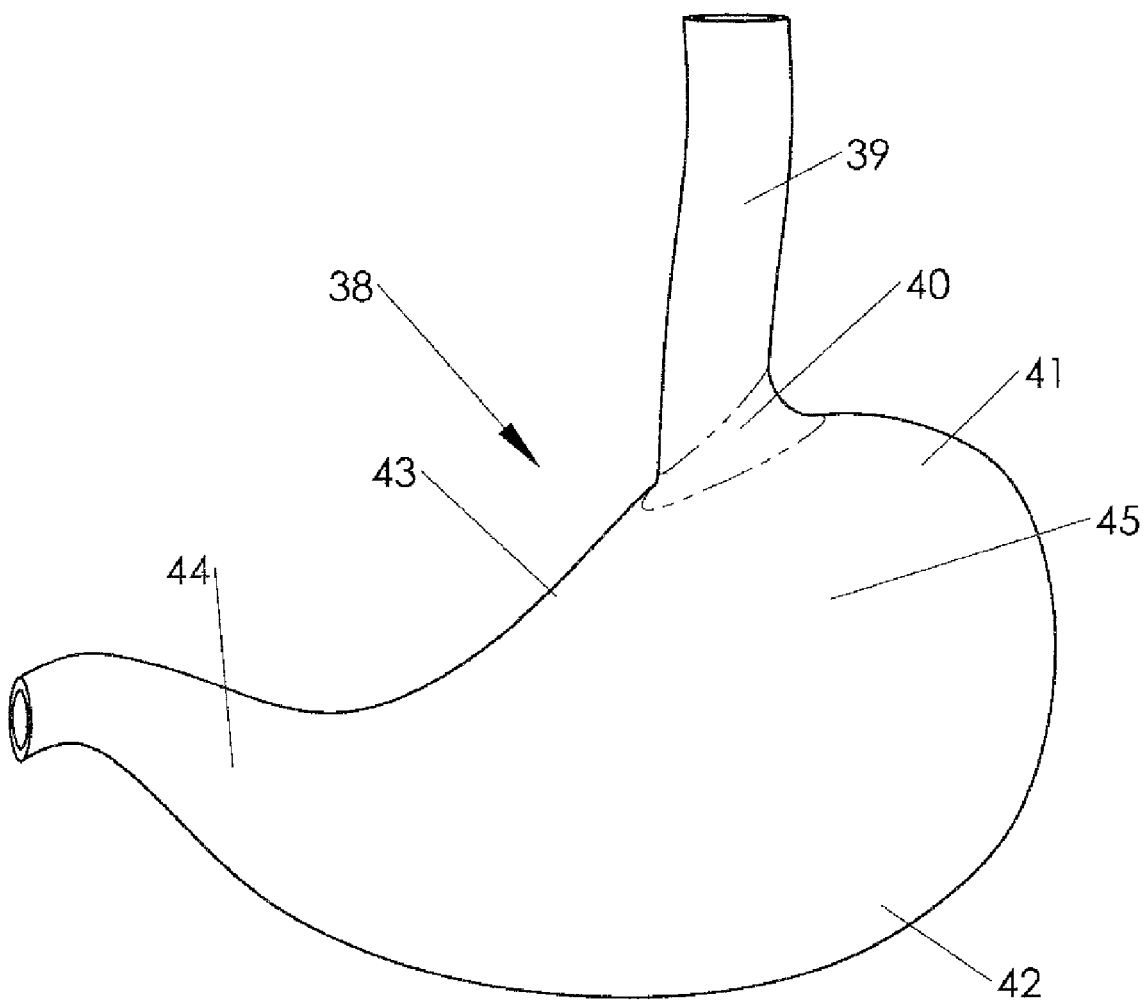
FIG. 16 is a front view of a stomach.

FIG. 16 is a front view of a stomach 38 and a distal portion of the esophagus 39. The gastroesophageal junction 40 is the region in which the esophagus connects to the stomach. Also labeled in FIG. 16 are the fundus 41, the greater curvature 42, the lesser curvature 43, the antrum 44 and the anterior wall 45. The method which is enabled by the present invention involves creating a fold in the wall of stomach 38 in such a way that multiple regions of the outer surface of the stomach are brought into apposition with one another and then fixated.

Figure 17:
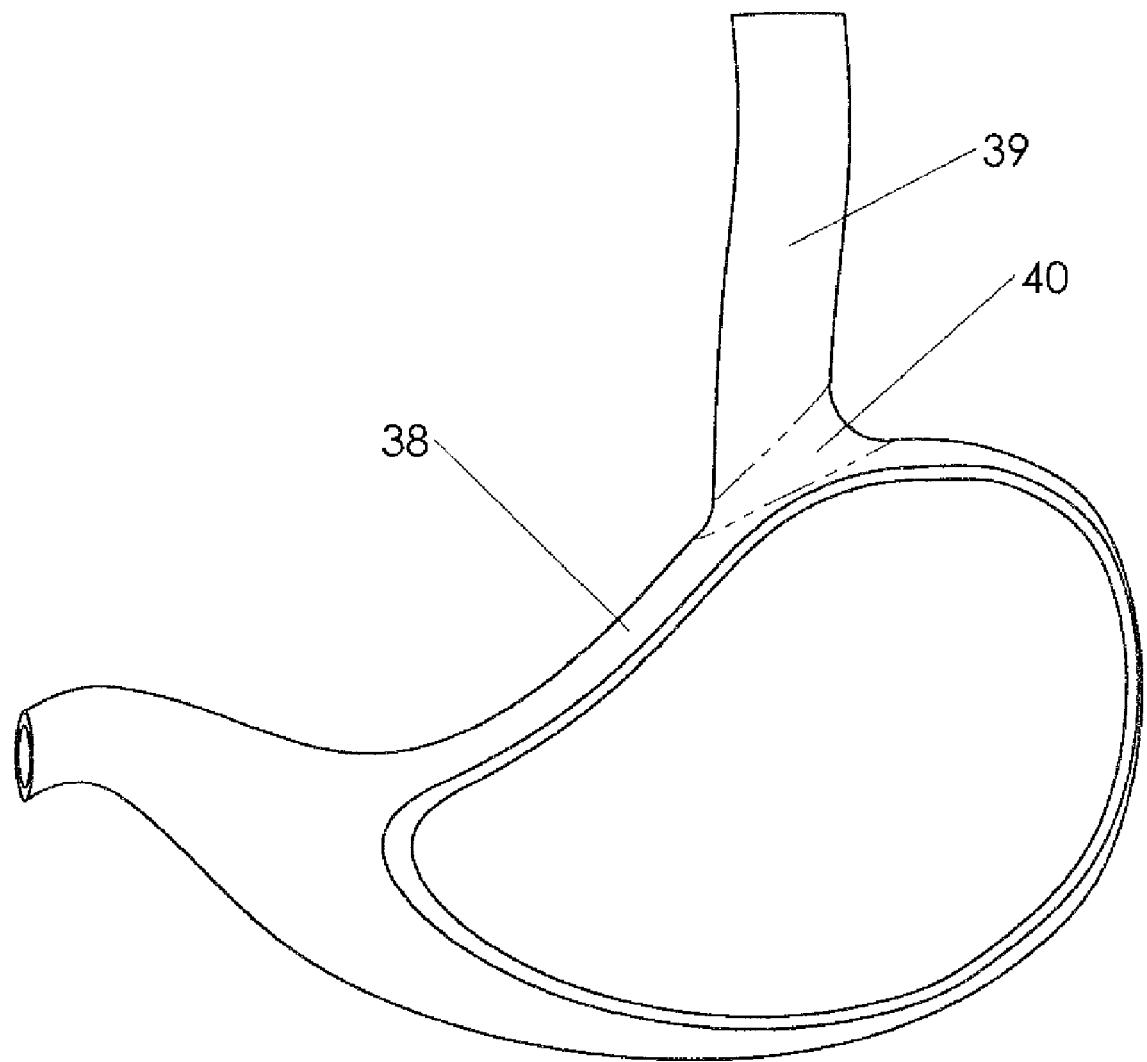
FIG. 17 is a cut-away front-view of a stomach.

FIG. 17 is a front view of stomach 38 and distal portion of esophagus 39, in which a portion of anterior wall 45 has been sectioned, revealing a cut-away view of the stomach wall and a view of the interior of stomach 38.

Figure 17A:
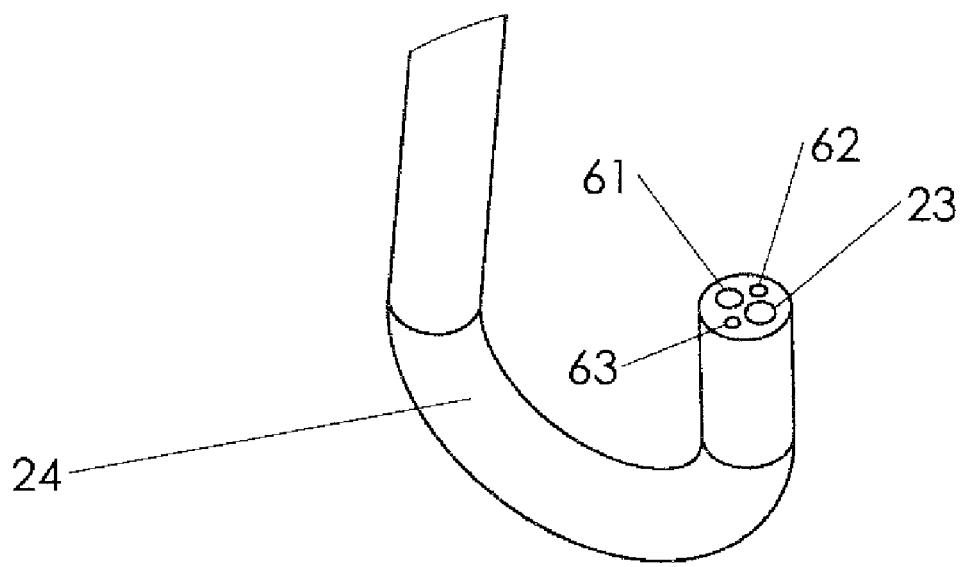
FIG. 17A is a perspective view of the distal end of a flexible endoscope.

FIG. 17A shows the distal end of flexible endoscope shaft 24. Endoscope shaft 24 has a proximal end and a distal end which is positionable within stomach 38. Working channel 23 is used to pass devices through the endoscope and into stomach 38. Endoscope lens 61 is used to transmit the endoscopic view within the organ to a video processor and video display outside the body, for viewing by the operator. Endoscope lens 61 may be at the distal end of a fiber optic bundle, or it may be a CCD chip, both of which are known in the art. Endoscope light source 62 is used to illuminate the viewing area. Distention/irrigation port 63 is used to inflate the stomach with air and clean endoscope lens 61.

Figure 17B:
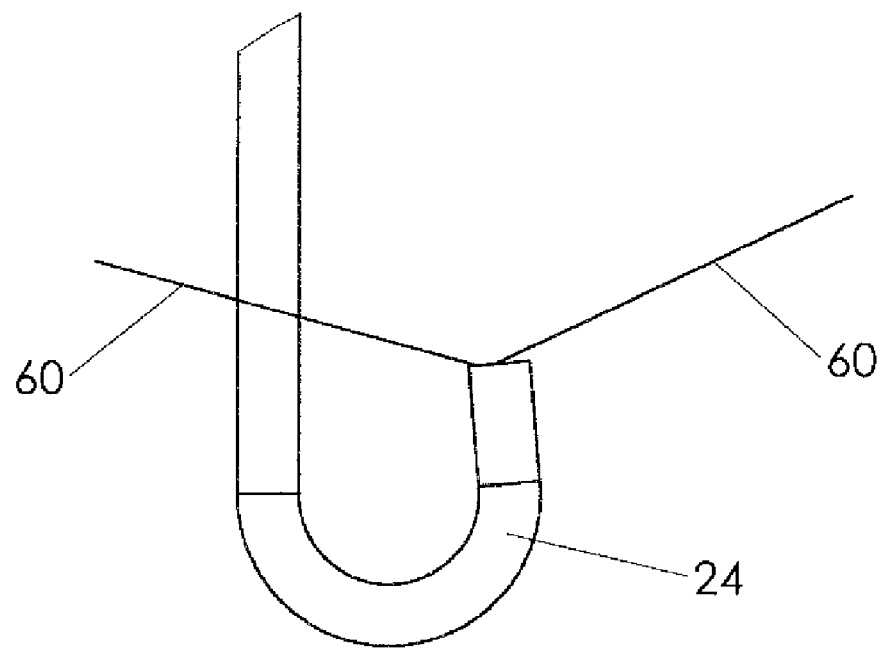
FIG. 17B is a side view of the distal end of a flexible endoscope.

FIG. 17B shows a side view of the distal end of flexible endoscope shaft 24. Lines 60 represent the endoscopic viewing region. This is the region beyond the distal end of flexible endoscope shaft 24 which can be viewed using endoscope lens 61 and the video processor and video display. Lines 60 represent a three-dimensional region that is approximately conical in shape, with the apex of the cone located at lens 61. The conical region essentially does not have a base, as objects, items or features can be visualized a great distance away from lens 61. Modern endoscopes provide viewing an area encompassed by an included angle of approximately 100 to 160 degrees, which would be the angle between the two lines 60 in FIG. 17B.

Figure 18:
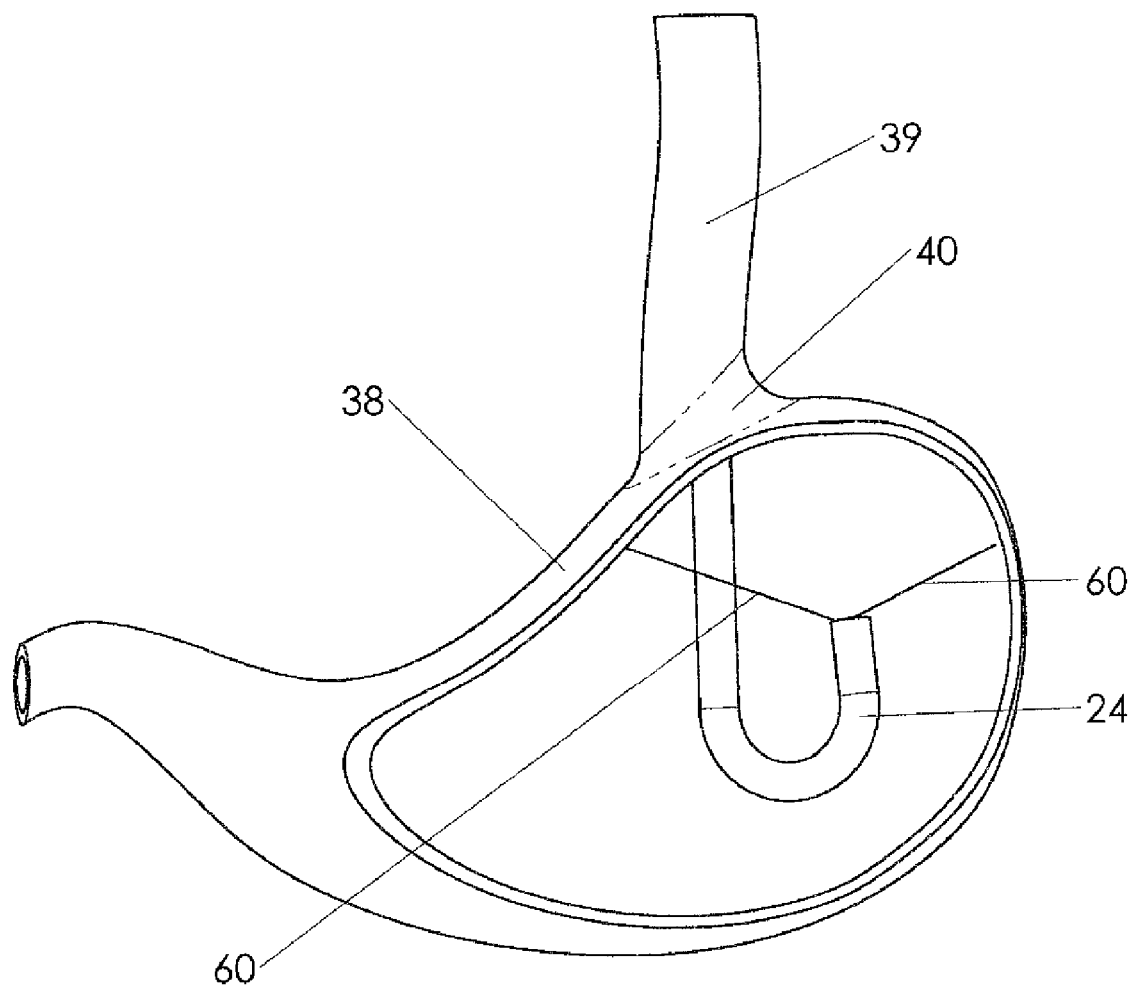
FIG. 18 is a cut-away front-view of a stomach with an endoscope in place.
Figure 19:
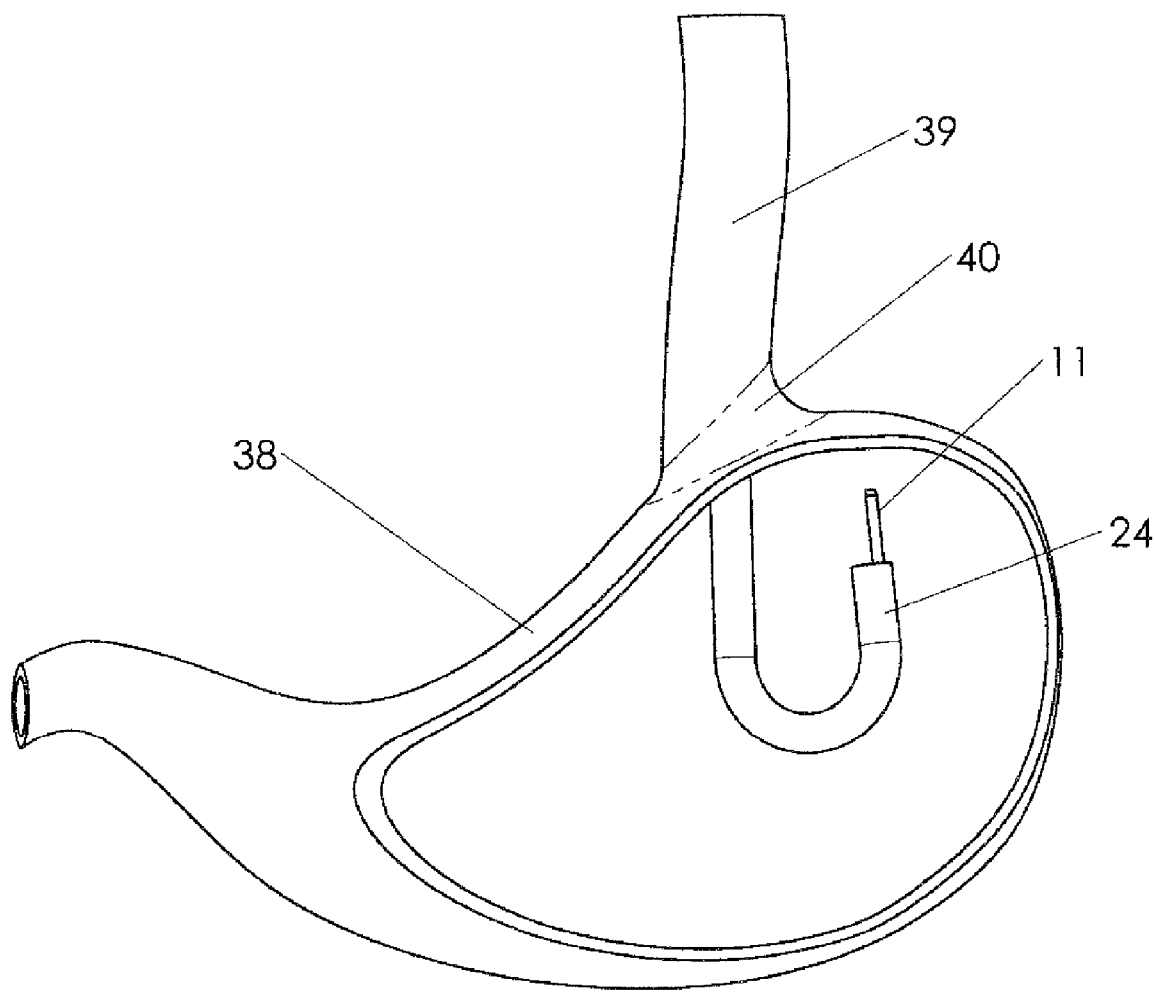
FIG. 19 is a cut-away front-view of a stomach with an endoscope in place and a tube extending from the distal end of the endoscope.

FIG. 18 shows the cut-away view of stomach 38 and the distal portion of esophagus 39 with the distal end of flexible endoscope shaft 24. Flexible endoscope shaft 24 has been passed by the operator into the mouth, down the esophagus, through gastroesophageal junction 40 and into stomach 38. We will refer to this as a "gastroscopic approach". The distal end of flexible endoscope shaft 24 has been articulated so that an interior view of gastroesophageal junction 40 and the surrounding region of the interior surface of the stomach wall is obtained. Lines 60 depict an approximation of the region which can be viewed by lens 61. In FIG. 19 instrument shaft 11 has been inserted into flexible endoscope working channel 23 and advanced so that the distal end of instrument shaft 11 protrudes beyond the distal end of flexible endoscope shaft 24. In this position the endoscope and instrument shaft 11 may be positioned to aim instrument shaft 11 at the desired first location for piercing the stomach wall. In another embodiment instrument shaft 11 is inserted through the esophagus and into the stomach next to the endoscope, rather than through the endoscope working channel. In another embodiment instrument shaft 11 is inserted through an overtube, rather than through the endoscope working channel. The overtube may have separate channels for the endoscope and instrument shaft 11. In this case the overtube can provide support for instrument shaft 11 within the esophagus and the stomach, to facilitate pushing, pulling, rotating, and/or otherwise repositioning or reshaping instrument shaft 11. The overtube may have articulation means, as is known in the art, to enable it to be angled, shaped, bent, articulated, etc. as desired. The overtube may have an opening in its wall that allows the endoscope to be angled away from instrument shaft 11. This hole may be, for example, five to 10 centimeters back from the distal end of the overtube. Advancing the distal end of the endoscope through the hole in the wall of the overtube allows the endoscope to move away from instrument shaft 11, in order to better visualize regions of the interior surface of the stomach wall.

Figure 20:
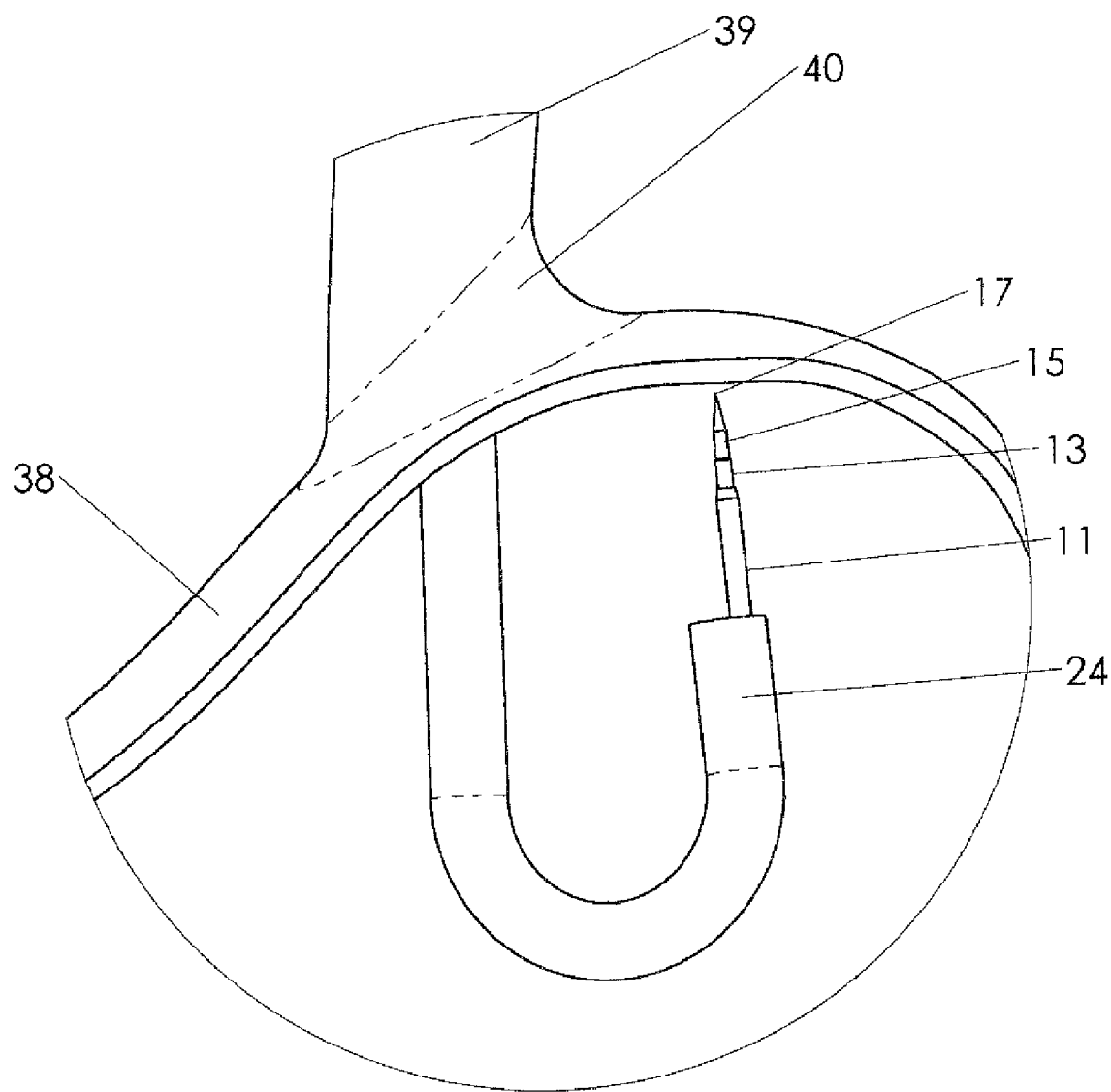
FIG. 20 is a cut-away front-view of a stomach with an endoscope in place and a tube and piercing element extending from the distal end of the endoscope.
Figure 21:
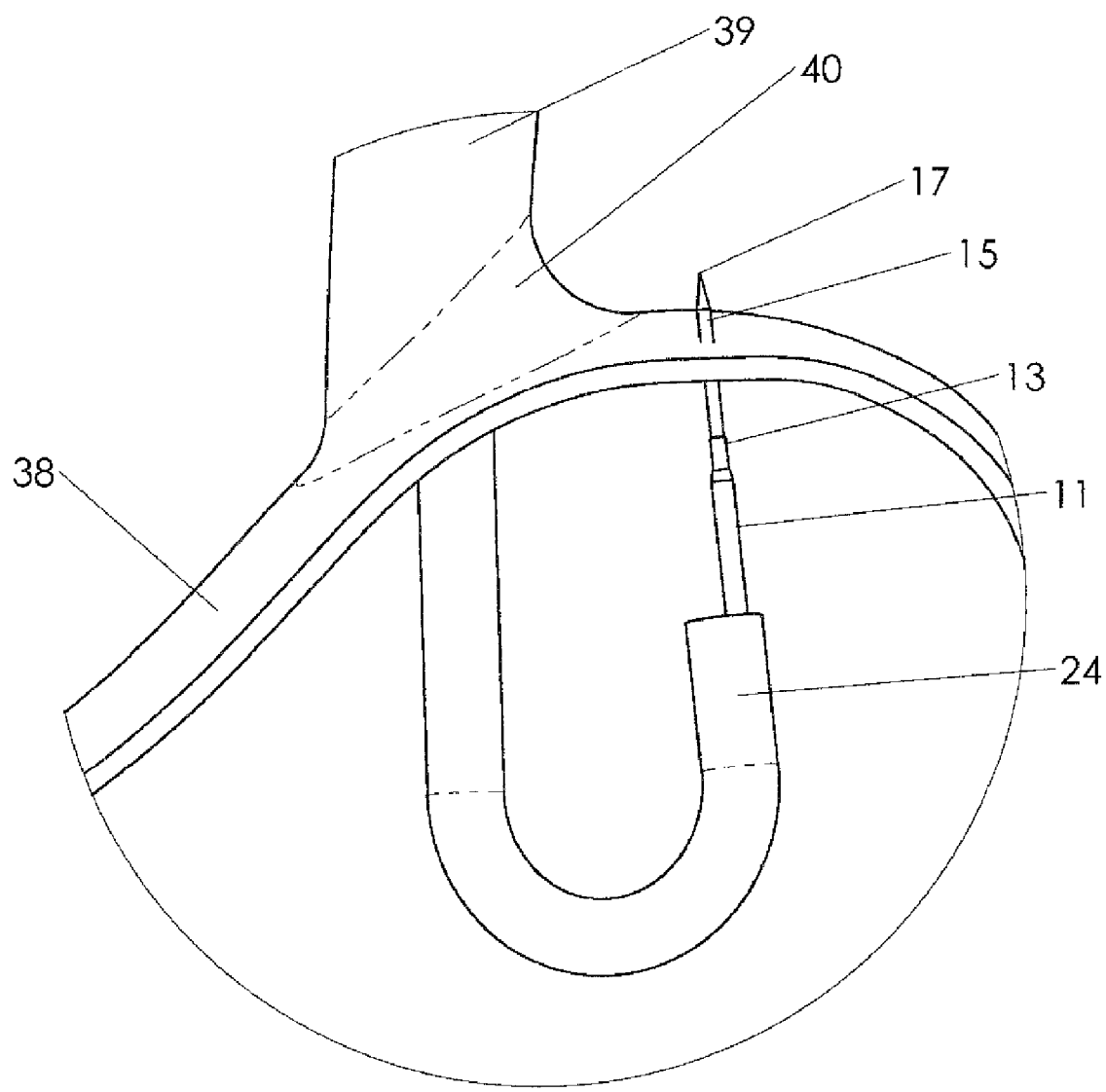
FIG. 21 is a cut-away front-view of a stomach with an endoscope in place and a tube extending from the distal end of the endoscope and a piercing element extending from the tube and through the wall of the stomach at a first location.

In FIG. 20 inner tube 13 has been advanced through the lumen of the instrument shaft 11, and piercing element 15 has been advanced through the lumen of inner tube 13, such that distal end 17 of piercing element 15 and distal end of inner tube 13 protrude beyond the distal end of instrument shaft 11. In FIG. 21 piercing element 15 has been advanced through the wall of stomach 38 such that distal end 17 of piercing element 15 is now outside the stomach 38. In one embodiment the advancement of piercing element 15 through the wall of stomach 38 is accomplished by pushing sharpened distal end 17 of piercing element 15 through the wall of stomach 38. In another embodiment the advancement of piercing element 15 through the wall of stomach 38 is accompanied by the application of electrical current to cauterize the tissue, in which case distal end 17 of piercing element 15 may be sharp or blunt. A blunt distal end 17 of piercing element 15 helps prevent piercing element 15 from injuring structures outside stomach 38. In another embodiment a tool is used to stabilize the stomach wall when piercing element 15 is advanced through the tissue. Examples of tools that may be used for this purpose include endoscopic forceps, a helical or "corkscrew" type retractor, and a cylindrical cap on the end of the endoscope which allows the tissue to be stabilized by positioning the open distal end of the cylinder against the tissue and applying suction via the endoscope, thus holding the tissue to the cylinder by suction. Other suitable tools that are known to someone skilled in the art may also be used. An endoscope with two working channels may be used to facilitate the use of a tissue stabilizing tool along with instrument 10.

Figure 22:
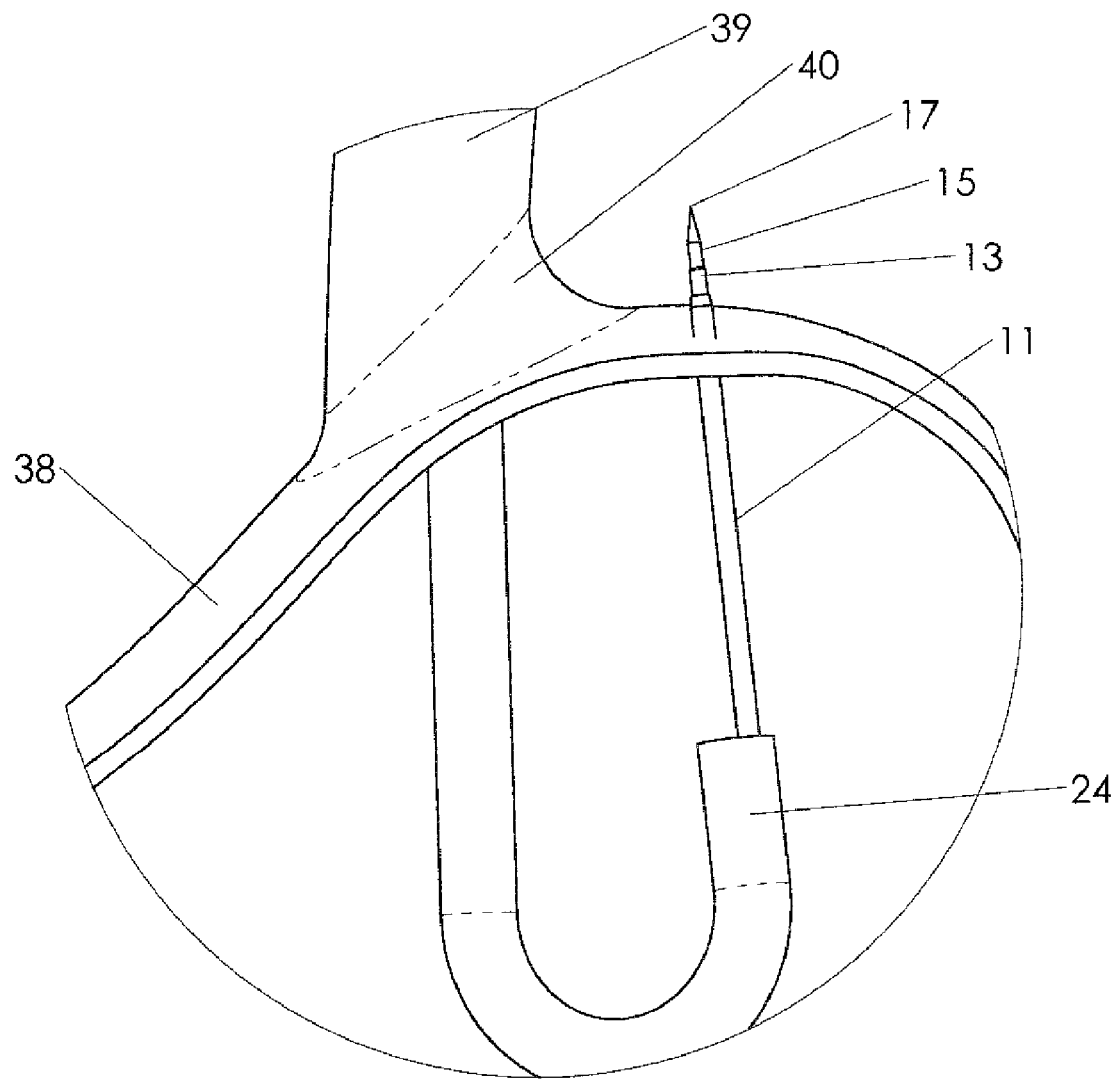
FIG. 22 is a cut-away front-view of a stomach with an endoscope in place and a tube and piercing element extending from the distal end of the endoscope and through the wall of the stomach at a first location.
Figure 23:
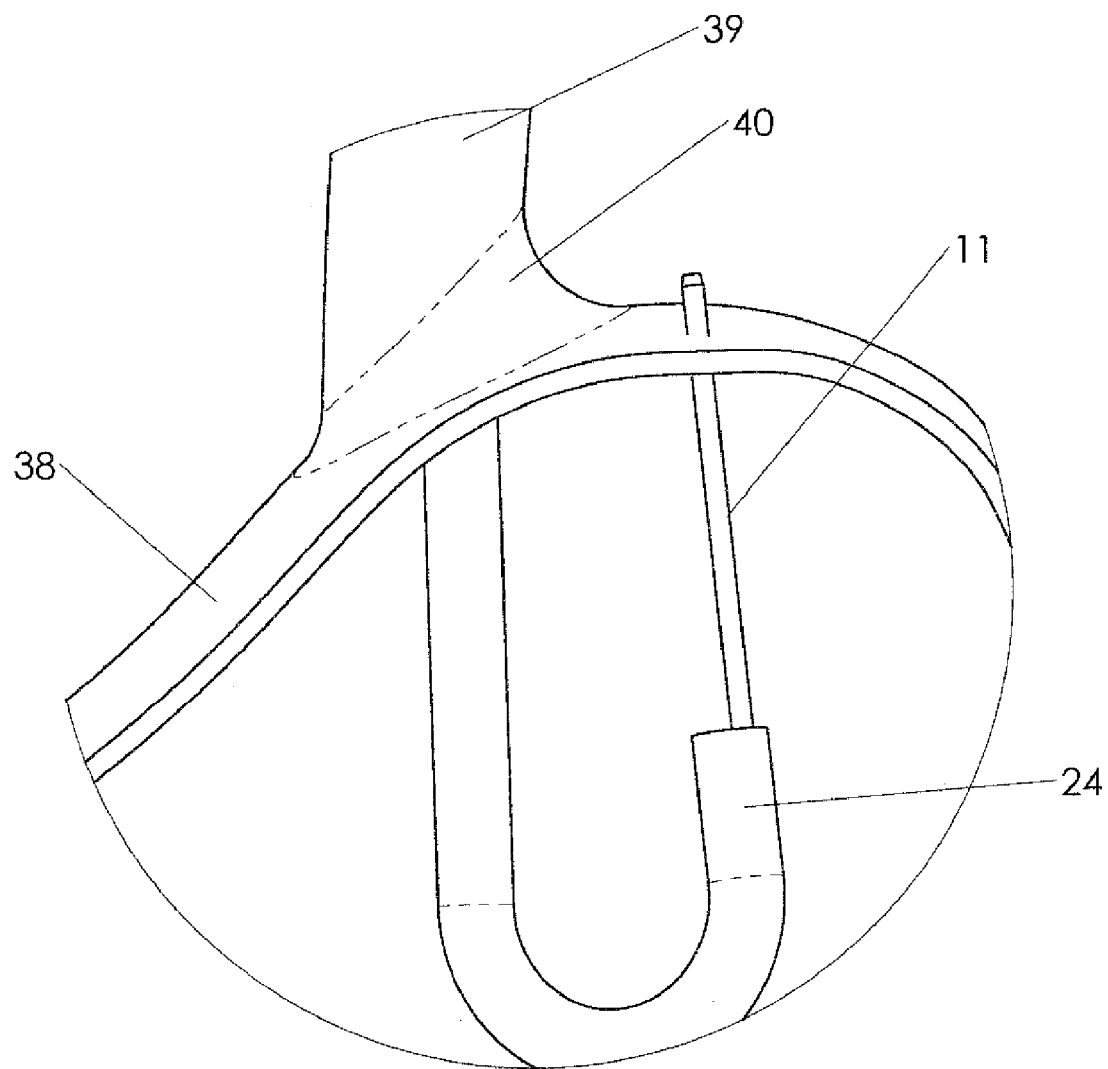
FIG. 23 is a cut-away front-view of a stomach with an endoscope in place and a tube extending from the distal end of the endoscope and through the wall of the stomach at a first location.
Figure 24:
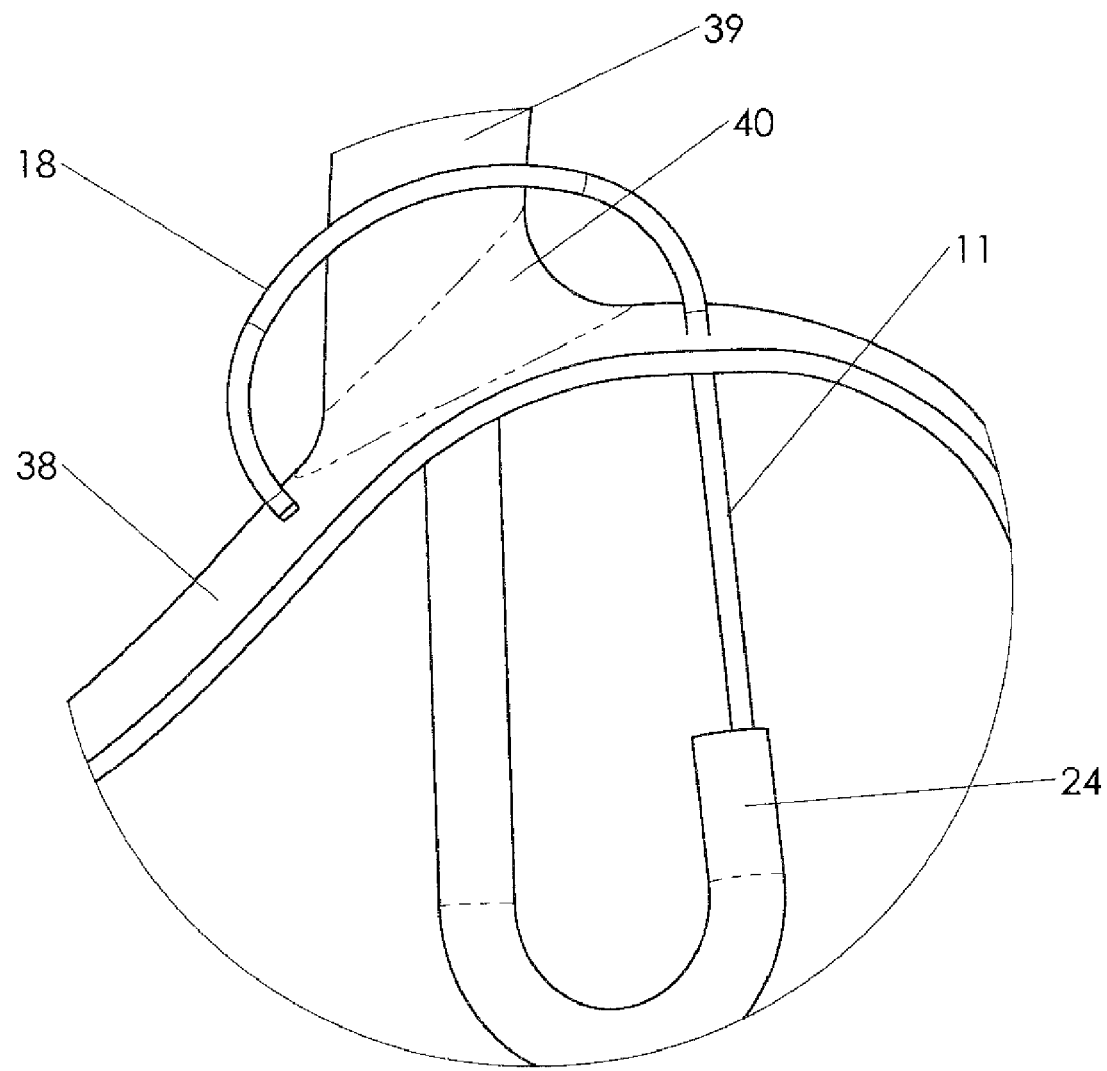
FIG. 24 is a cut-away front-view of a stomach with an endoscope in place and a tube extending from the distal end of the endoscope and through the wall of the stomach at a first location and advanced so that the distal end of the tube is adjacent to the wall of the stomach at a second location.
Figure 25:
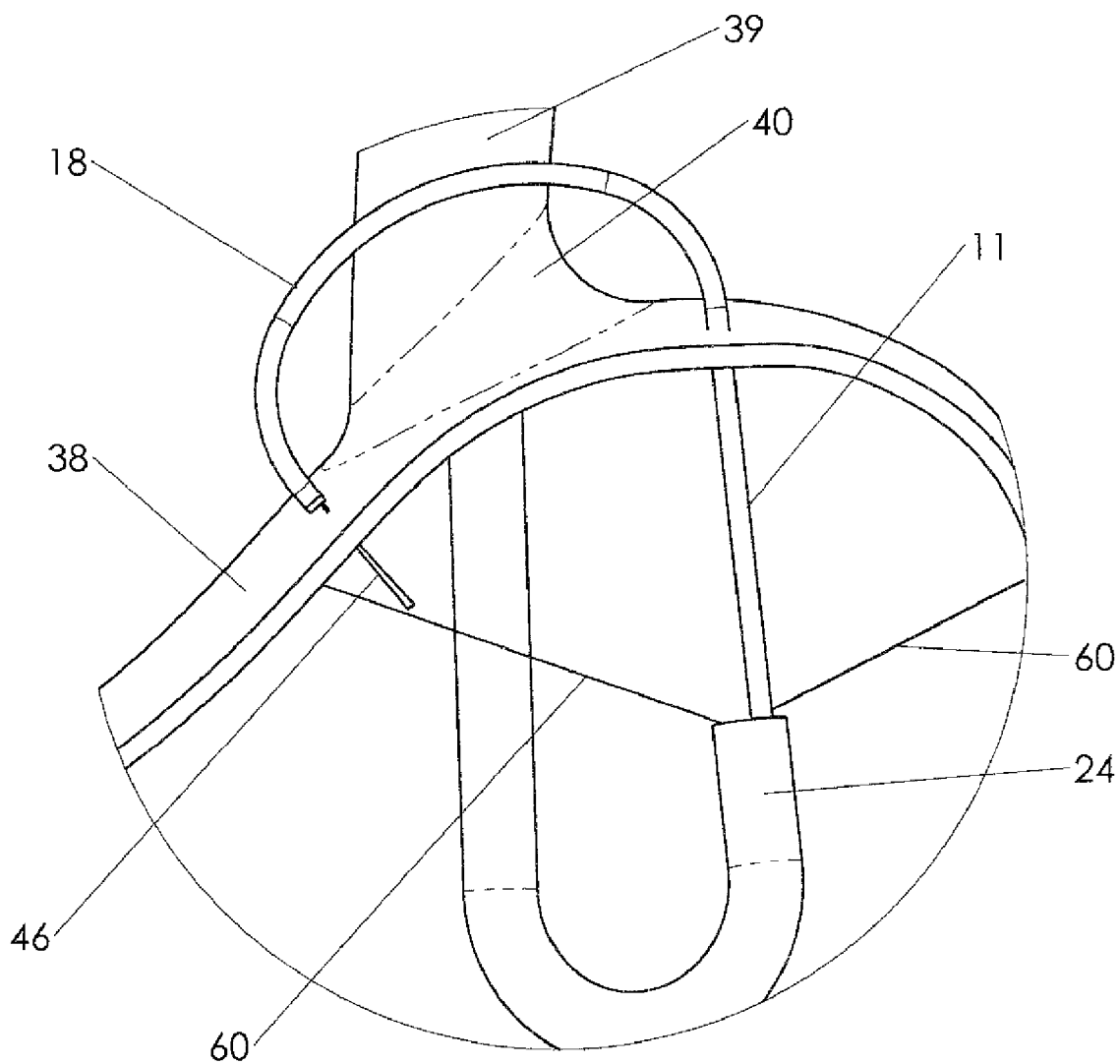
FIG. 25 is a cut-away front-view of a stomach with an endoscope in place and a tube extending from the distal end of the endoscope and through the wall of the stomach at a first location and advanced so that the distal end of the tube is adjacent to the wall of the stomach at a second location, and with light being emitted from the distal end of the tube and shining through the wall of the stomach at the second location.
Figure 26:
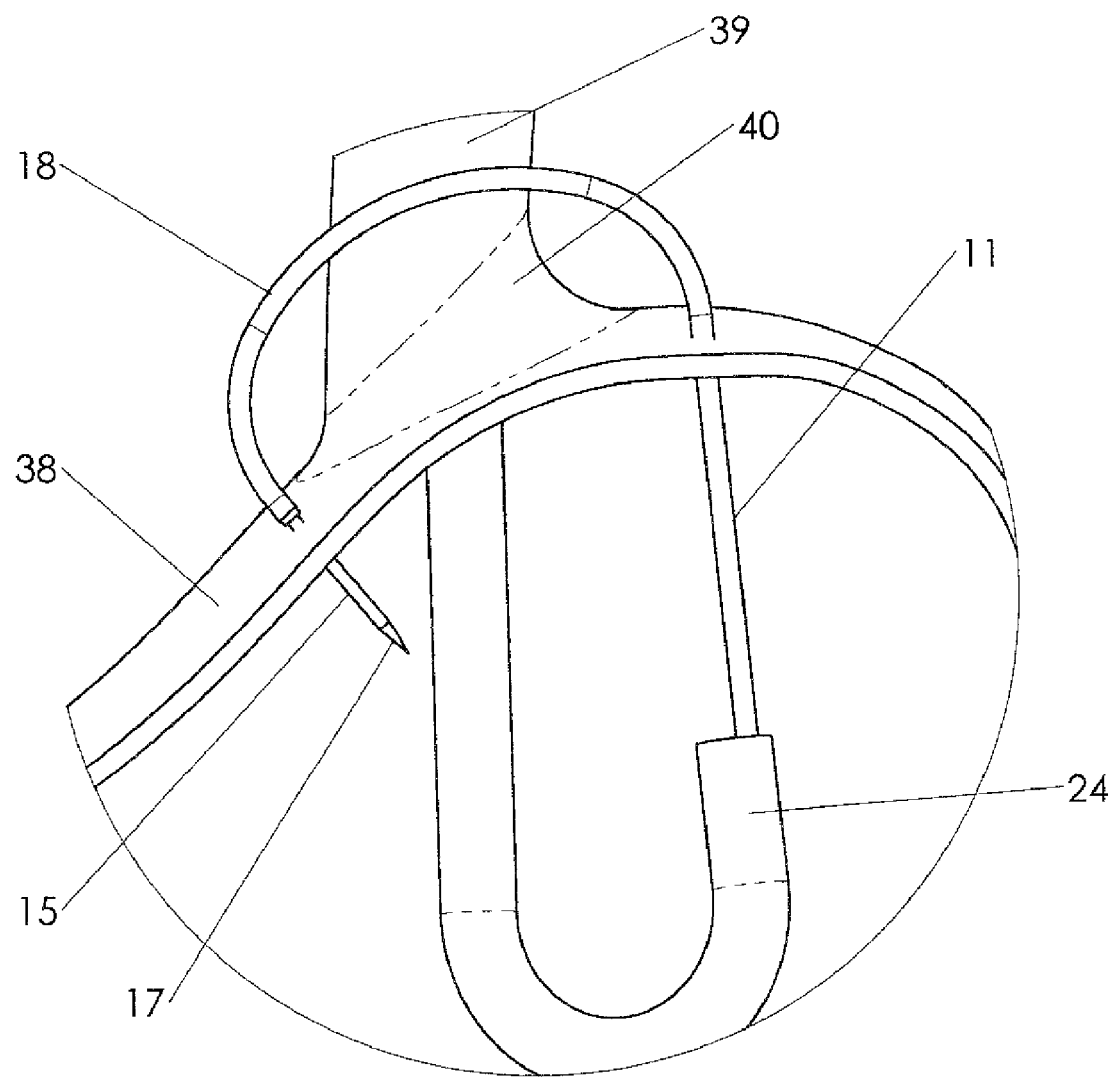
FIG. 26 is a cut-away front-view of a stomach with an endoscope in place and a tube extending from the distal end of the endoscope and through the wall of the stomach at a first location, and a piercing element extending from the tube and through the wall of the stomach at a second location.
Figure 27:
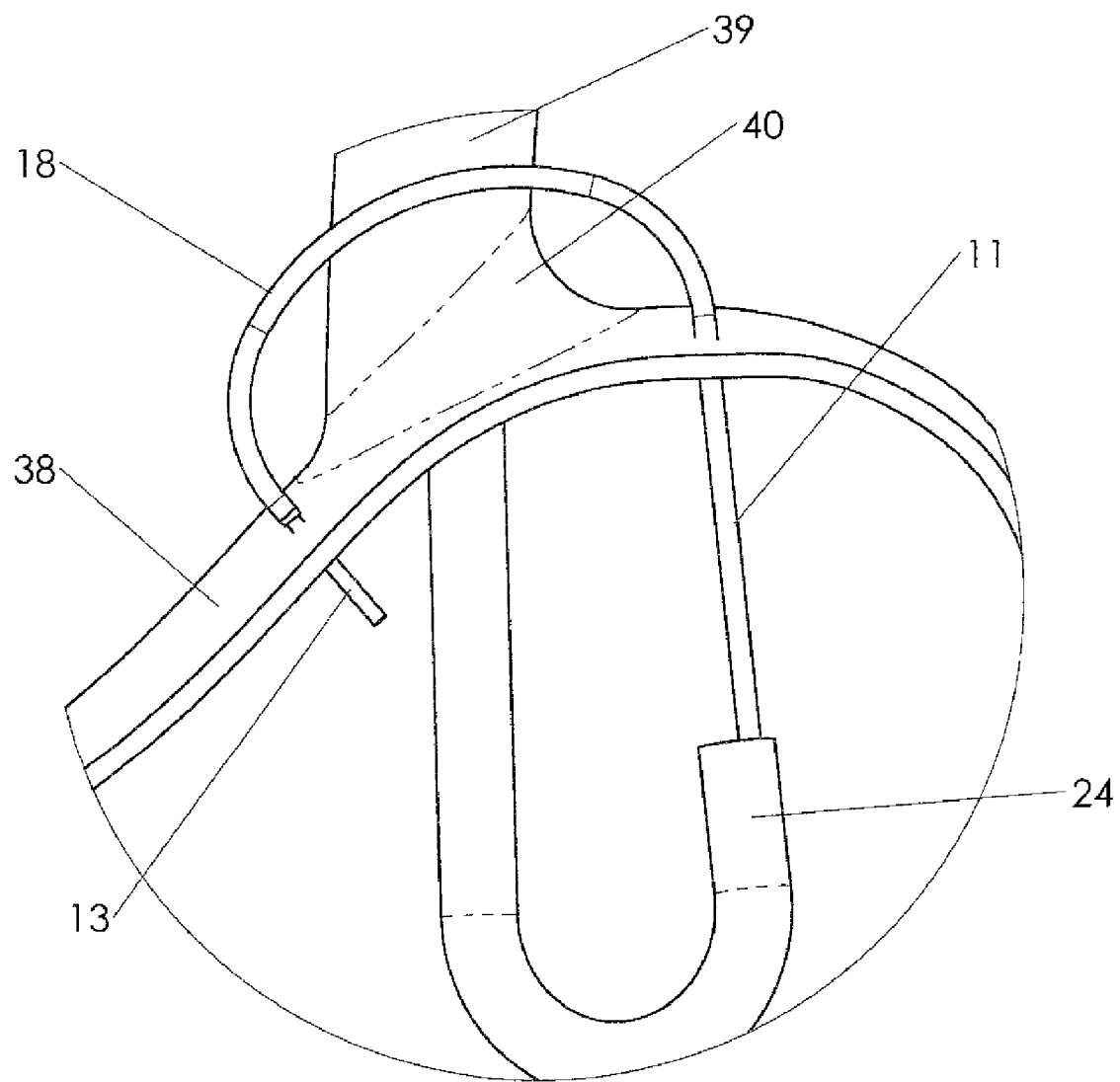
FIG. 27 is a cut-away front-view of a stomach with an endoscope in place and a first tube extending from the distal end of the endoscope and through the wall of the stomach at a first location and, and a second tube extending from the first tube and through the wall of the stomach at a second location.
Figure 28:
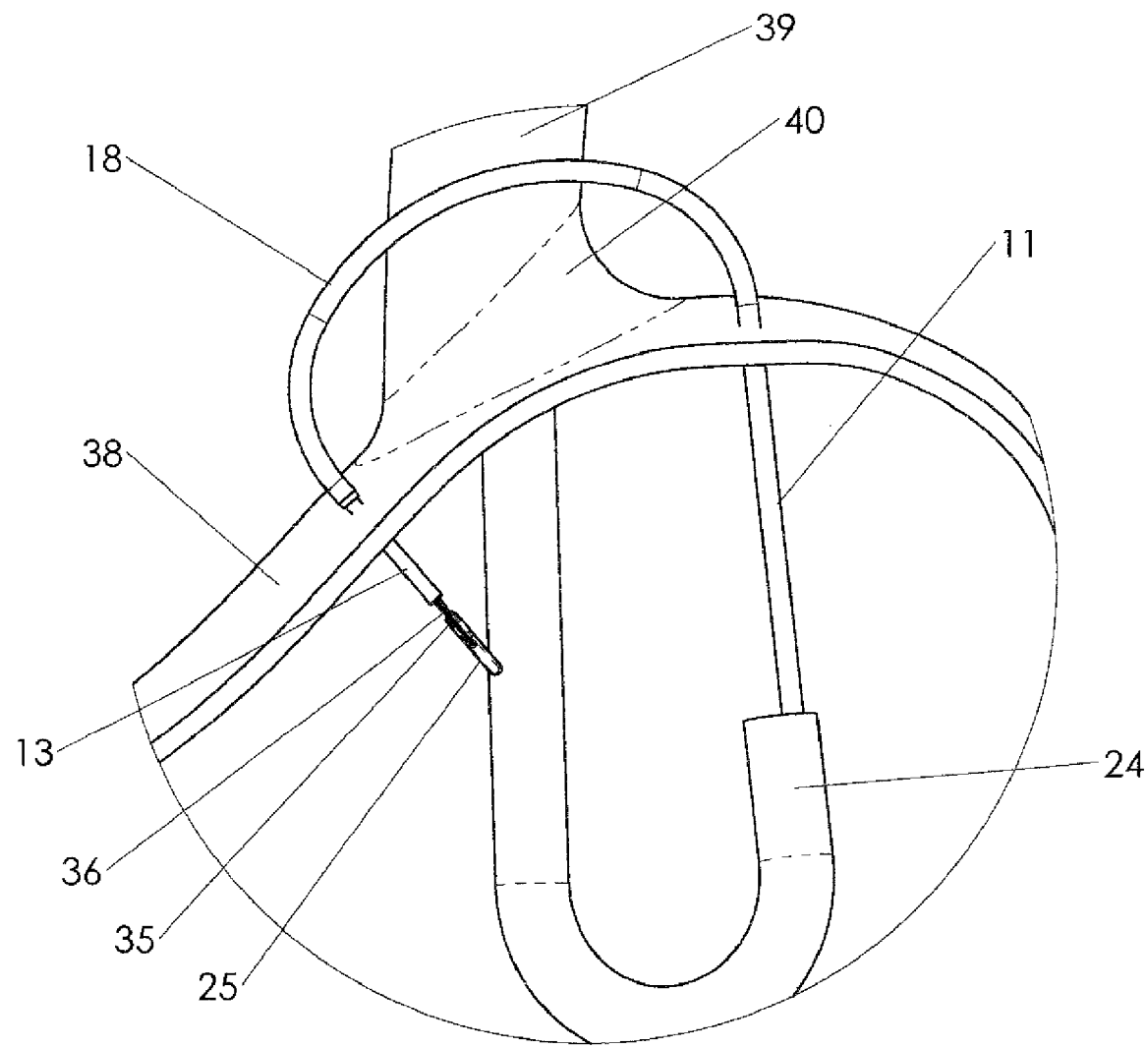
FIG. 28 is a cut-away front-view of a stomach with an endoscope in place and a first tube extending from the distal end of the endoscope and through the wall of the stomach at a first location and, a second tube extending from the first tube and through the wall of the stomach at a second location, and a tissue anchor extending from the distal end of the second tube.
Figure 29:
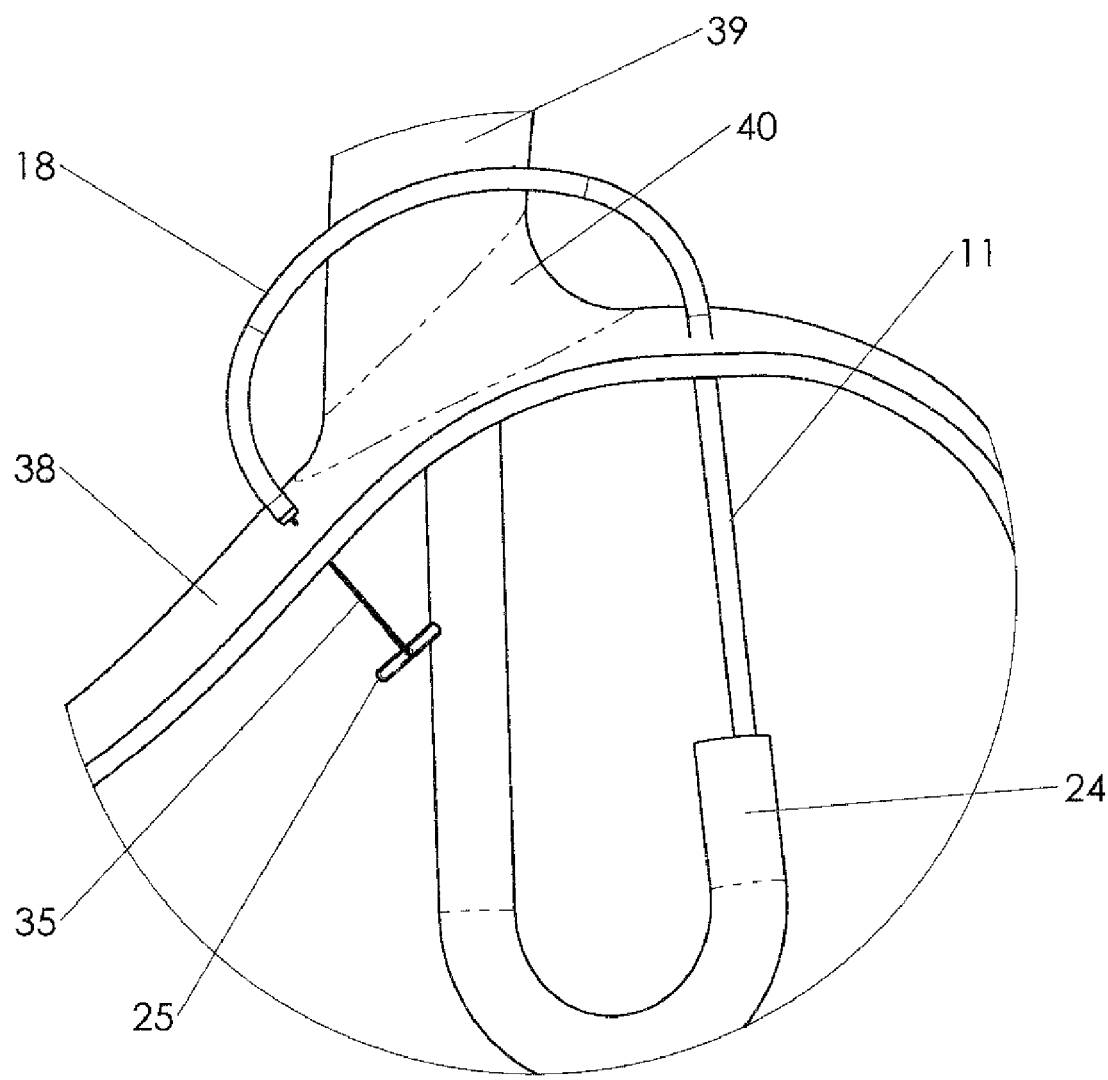
FIG. 29 is a cut-away front-view of a stomach with an endoscope in place and a first tube extending from the distal end of the endoscope and through the wall of the stomach at a first location and, a second tube extending from the first tube and through the wall of the stomach at a second location, and a tissue anchor extending from the distal end of the second tube and configured for tissue fixation.
Figure 30:
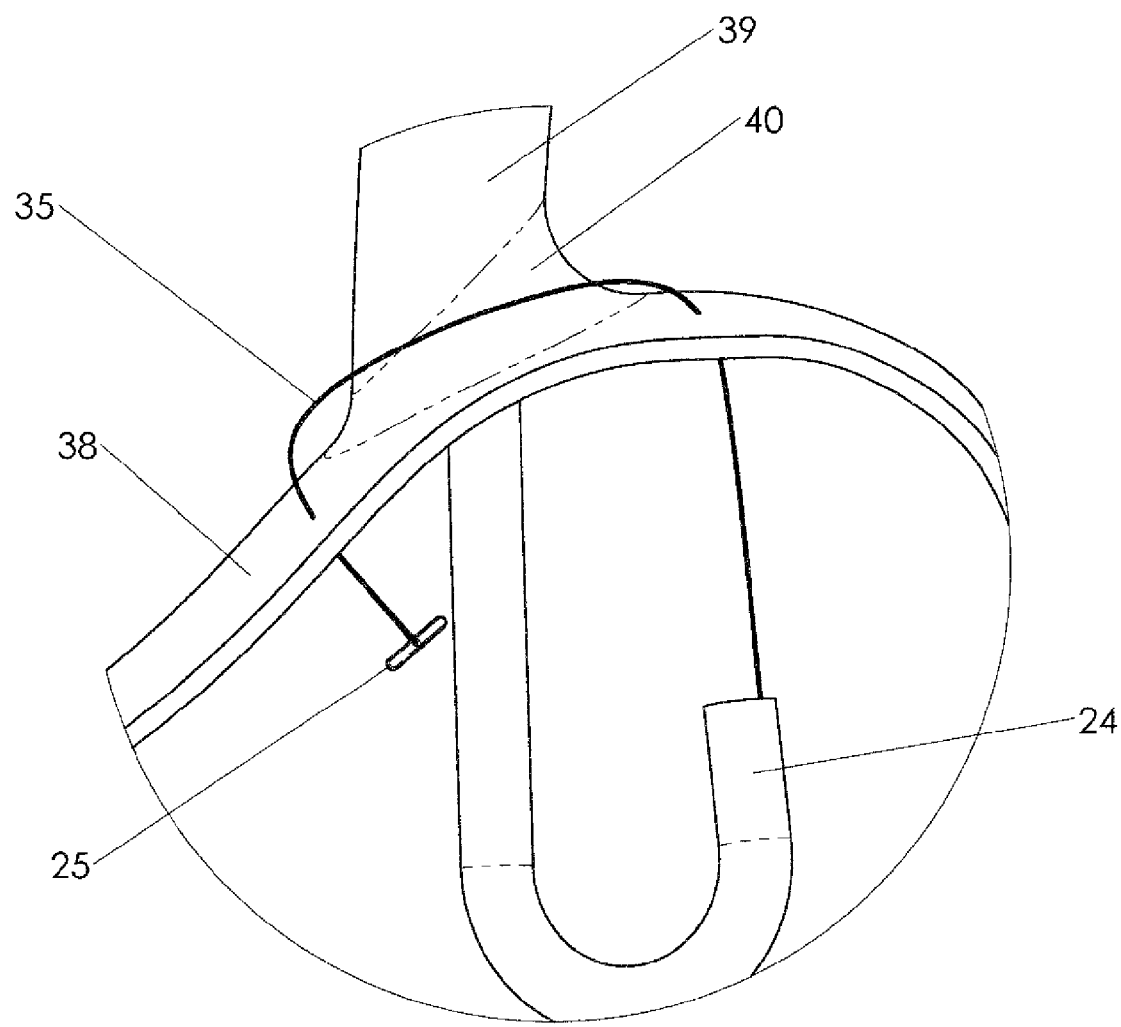
FIG. 30 is a cut-away front-view of a stomach with an endoscope in place and a suture extending from the distal end of the endoscope and through the wall of the stomach at first and second locations, with a tissue anchor attached to the distal end of the suture.
Figure 31:
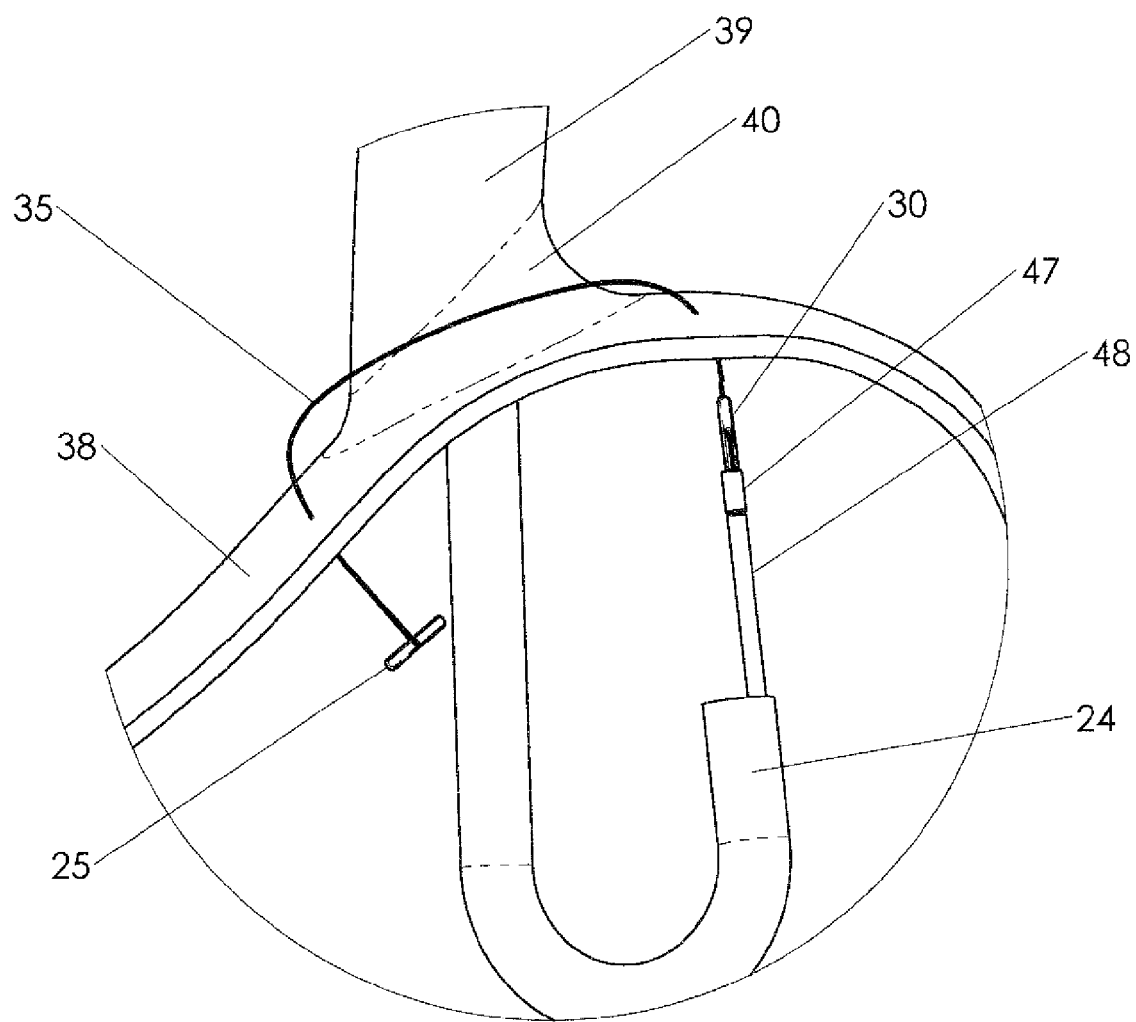
FIG. 31 is a cut-away front-view of a stomach with an endoscope in place and a suture extending from the distal end of the endoscope and through the wall of the stomach at first and second locations, a first tissue anchor attached to the distal end of the suture, and a second tissue anchor advancing over suture.
Figure 32:
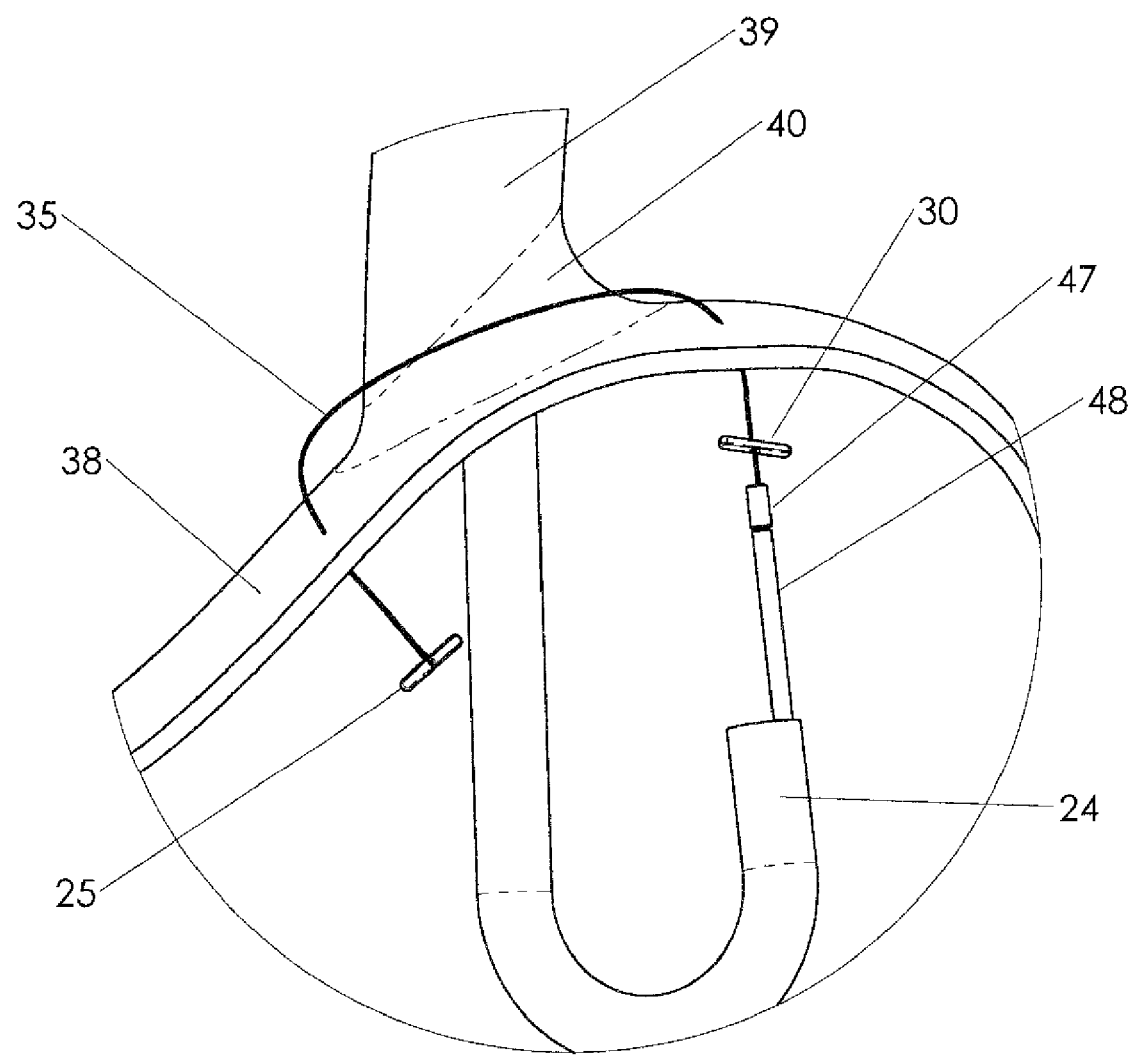
FIG. 32 is a cut-away front-view of a stomach with an endoscope in place and a suture extending from the distal end of the endoscope and through the wall of the stomach at first and second locations, a first tissue anchor attached to the distal end of the suture, and a second tissue anchor advancing over suture and configured to fixate tissue.

In FIG. 22 the instrument shaft 11 has been advanced through the hole in the stomach wall that was created by piercing element 15. In FIG. 23 piercing element 15 and inner tube 13 have been withdrawn so that the distal end of each is within instrument shaft 11. In FIG. 24 instrument shaft 11 has been advanced through the hole in the stomach wall such that articulating section 18 is positioned outside stomach 38, and articulating section 18 has been articulated. As piercing element 15 has been retracted, and the distal end of instrument shaft 11 is blunt, positioning the distal end of instrument shaft 11 outside stomach 38 does not damage any structures outside stomach 38. In FIG. 25 the light source has been activated, and the light shining from distal end 20 of the light source shines through the wall of stomach 38. In FIG. 25 reference number 46 indicates a graphical representation of the light shining through the wall of stomach 38 and into the inside of stomach 38. The position of the distal end of instrument shaft 11 can be determined by visualizing with the endoscope the light shining through the wall of stomach 38. Lines 60 represent the endoscopic viewing region. As light 46 is within the endoscopic viewing region defined by lines 60, light 46 may be visualized by the operator. A region of light is visualized on the interior wall of stomach 38, indicating that the distal end of instrument shaft 11 is located at the exterior of the stomach in the vicinity indicated by the light. In this embodiment light 46 is a location indicator, and the endoscope is an optical receiver. The endoscope light source may be set to a dimmer setting, or shut off entirely, to aid visualization of light 46. In another embodiment an alternate location indicator is the distal end of instrument shaft 11 pushing against the stomach wall from outside stomach 38. The stomach wall is visualized with the endoscope, and inward movement of the stomach wall at a particular location indicates that the distal end of instrument shaft 11 is located at the exterior of the stomach in the vicinity indicated by the inwardly moved stomach wall. Once the location of the distal end of instrument shaft 11 has been detected using the location indicator and the optical receiver the endoscope and instrument shaft 11 may be manipulated to position the distal end of instrument shaft 11 in proximity to the stomach wall at the desired second location for piercing the stomach wall. Manipulation may include advancing, withdrawing, rotating, articulating, straightening or otherwise moving or reshaping instrument shaft 11. As the distal end of instrument shaft 11 is blunt and atraumatic, the distal end of instrument shaft 11 does not involve any organs or tissues outside of the stomach, but rather it simply moves past them as it is manipulated. Visualization from within the stomach of the light shining at the distal end of instrument shaft 11 also ensures that organs or tissues outside of the stomach are not involved in the tissue manipulation or fixation. Piercing element 15 is then advanced through the wall of the stomach from the outside to the inside at the second location, as shown in FIG. 26. The various embodiments of advancing piercing element 15 through the wall of stomach 38 as previously described for advancing piercing element through the wall of stomach 38 at the first location also apply in piercing at the second location. In FIG. 27 inner tube 13 has been advanced over piercing element 15 and through the hole in stomach 38 at the second location. Piercing element 15 has been retracted and removed from the lumen of inner tube 13. In FIG. 28 first tissue anchor 25 has been advanced through the lumen of inner tube 13. During this action first tissue anchor 25 is in a first state in which it is configured to pass through the lumen of inner tube 13. Pusher 36 has pushed first tissue anchor 25 beyond the distal end of inner tube 13, and into stomach 38. In FIG. 29 pusher 36 and inner tube 13 have been retracted, leaving first tissue anchor 25 and a portion of suture 35 in the stomach, with suture 35 passing through the hole in stomach 38 at the second location. In FIG. 29 first tissue anchor 25 is in a second state in which it is configured for tissue fixation. In FIG. 30 instrument shaft 11 has been retracted and removed from the working channel 23 of endoscope 22, leaving first tissue anchor 25 in the stomach 38, and suture 35, which is attached to first tissue anchor 25, passing through the holes in stomach 38 at second and first locations and through the working channel 23 of flexible endoscope 22. In FIG. 31 second tissue anchor component 30 and suture lock 47 have been advanced along suture 35 and through working channel 23 of endoscope 22, into stomach 38. Second tissue anchor component 30 and suture lock 47 taken in combination constitute a second tissue anchor. In FIG. 31 the second tissue anchor is shown in a first state in which it is configured to pass through working channel 23 of flexible endoscope 22 and is slideably engaged with suture 35. Anchor delivery device 48 advances the second tissue anchor through endoscope 22 working channel 23 and over suture 35. In FIG. 32 second tissue anchor component 30 is configured for tissue fixation, as it has rotated approximately 90 degrees relative to suture 35, and a relatively large surface area of second tissue anchor component 30 is presented in an orientation that will interact with the tissue.

Once the second tissue anchor has advanced beyond the distal end of flexible endoscope shaft 24, the second tissue anchor is further advanced while tension is maintained on suture 35. As the second tissue anchor is advanced first tissue anchor 25 presses against the inner surface of stomach 38 at the second location, and second tissue anchor component 30 presses against the inner surface of stomach 38 at the first location. First and second locations of stomach tissue are moved closer to one another until the outer surface of stomach 38 at the first location and the outer surface of stomach 38 at the second location are brought into apposition and are touching one another, thus creating a fold in the stomach wall. At this point suture lock 47 is locked onto suture 35, preventing second tissue anchor component 30 from retracting. Second tissue anchor is now in a state in which it is configured to fixate tissue and lock onto suture 35. Once suture lock 47 is locked first tissue anchor 25 and second tissue anchor component 30 clamp the first location of the stomach and the second location of the stomach together. The outer surface of the stomach at the first location and the outer surface of the stomach at the second location are clamped together, and will heal over time, creating a permanent fold in the wall of stomach 38. Once suture lock 47 is locked suture 35 is cut proximal to the second tissue anchor, using endoscopic scissors, a suture cutter or other methods known to one skilled in the art. In an alternate embodiment suture 35 includes an eyelet at its proximal end, positioned for example two centimeters from first tissue anchor 25. An additional suture is threaded through the eyelet, and doubled back, so that both lengths of the additional suture extend back through inner tube 13. The additional suture is used to apply tension to suture 35. Once suture lock 47 has been locked onto suture 35 the additional suture may be removed by simply pulling one end, and the additional suture feeds through the eyelet and out of the body. This embodiment eliminates the need for suture cutting.

Figure 33:
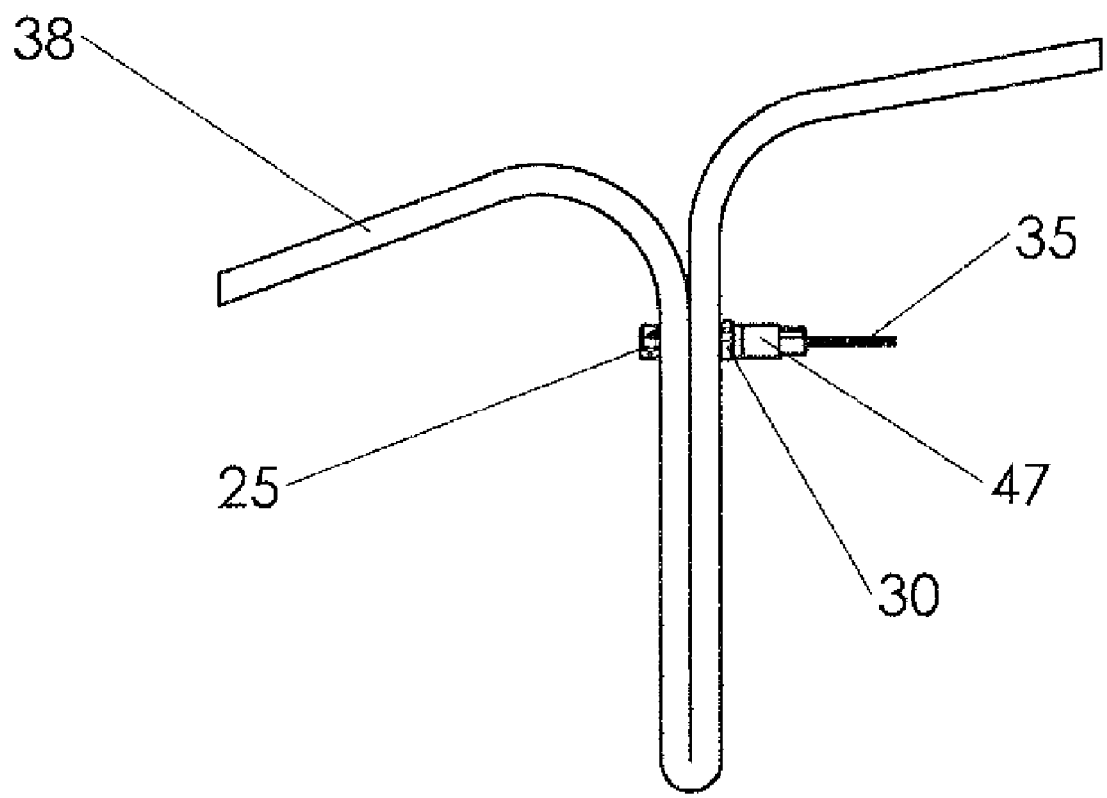
FIG. 33 is a cut-away view of folded stomach tissue fixated by a first tissue anchor, a suture and a second tissue anchor.
Figure 34:
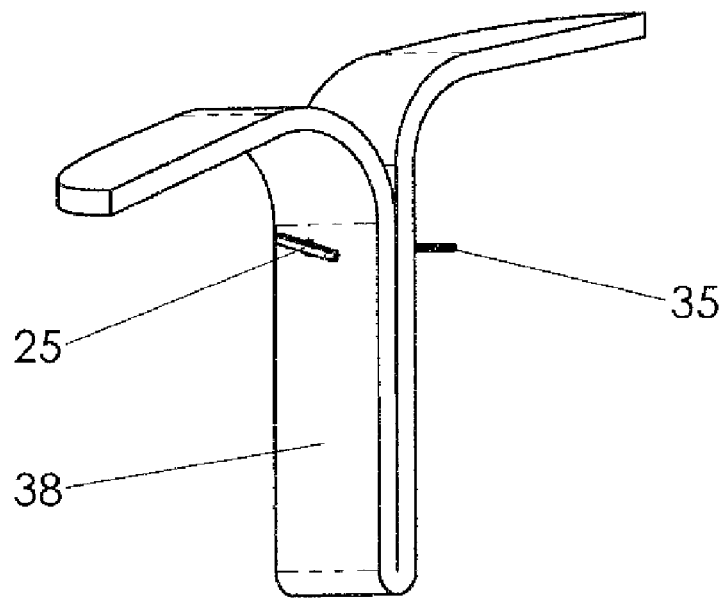
FIG. 34 is a cut-away perspective view of folded and fixated stomach tissue, showing a first tissue anchor.
Figure 35:
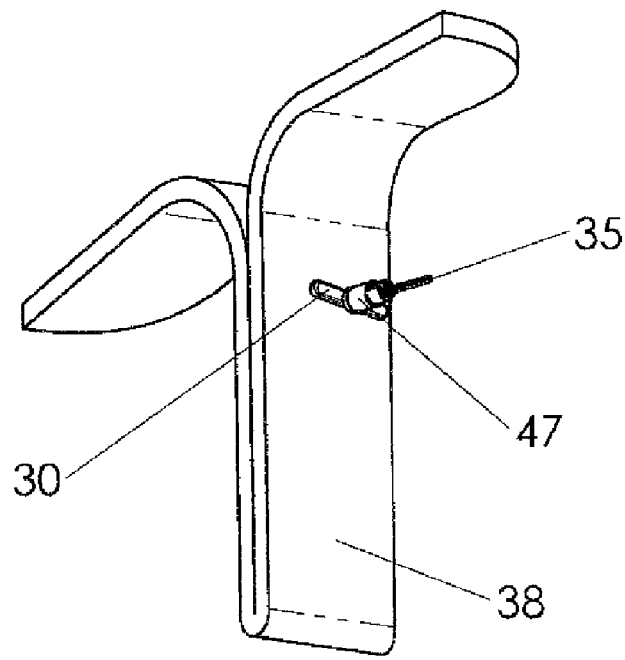
FIG. 35 is a cut-away perspective view of folded and fixated stomach tissue, showing a second tissue anchor.

FIG. 33 shows a cut-away view of the folded stomach tissue 38 fixated by first tissue anchor 25, suture 35 and second tissue anchor, consisting of second tissue anchor component 30 and suture lock 47. FIG. 34 shows a cut-away perspective view of the folded and fixated stomach tissue 38, in which first tissue anchor 25 and suture 35 are visible. FIG. 35 shows a cut-away perspective view of the folded and fixated stomach tissue 38 in which suture 35 and second tissue anchor, consisting of second tissue anchor component 30 and suture lock 47, are visible.

At this point the procedure is complete, and the endoscope may be withdrawn from the patient. Alternatively, the procedure may be completed to place additional tissue anchors and suture. Additional placements may augment the tissue fold to provide more secure tissue fixation. Additional placements may also increase the size of the tissue fold. Additional placements may also create additional tissue folds.

Figure 36:
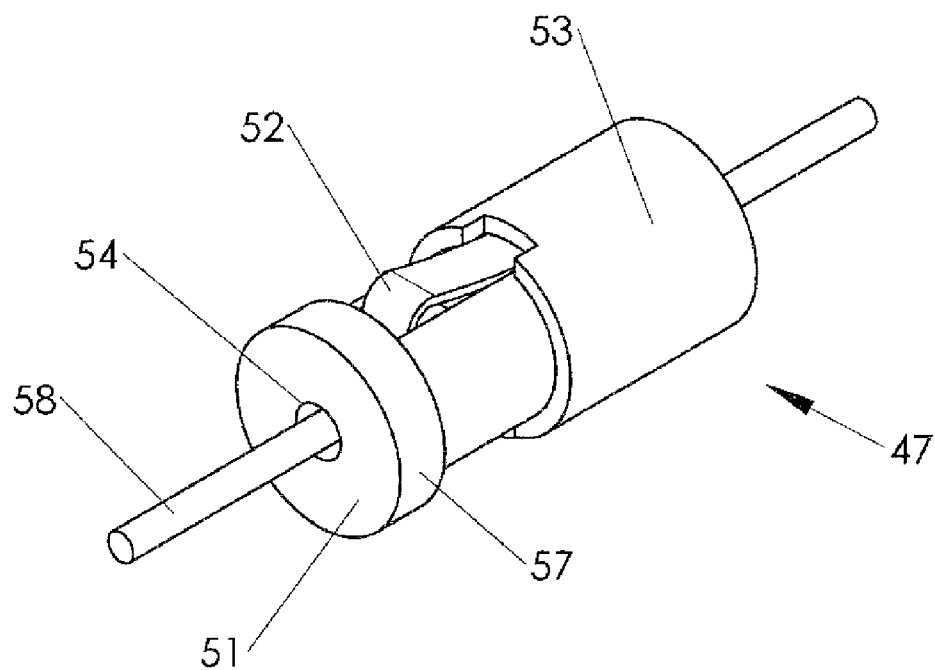
FIG. 36 is a perspective view of a suture lock.
Figure 37:
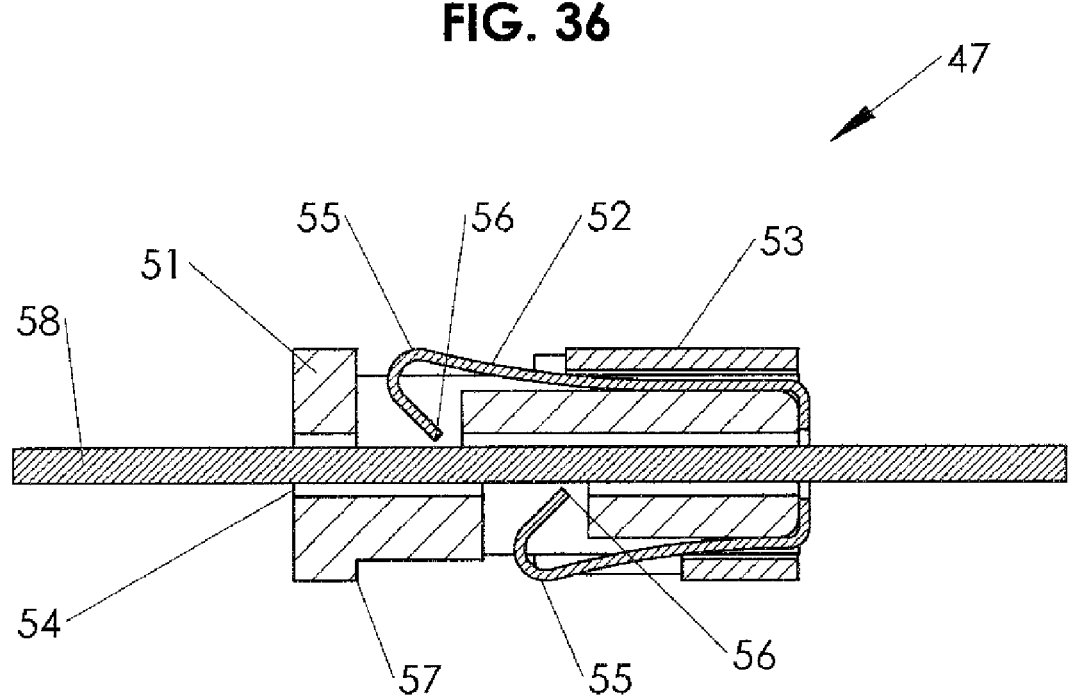
FIG. 37 is a cut-away view of a suture lock configured to slide over suture.
Figure 38:
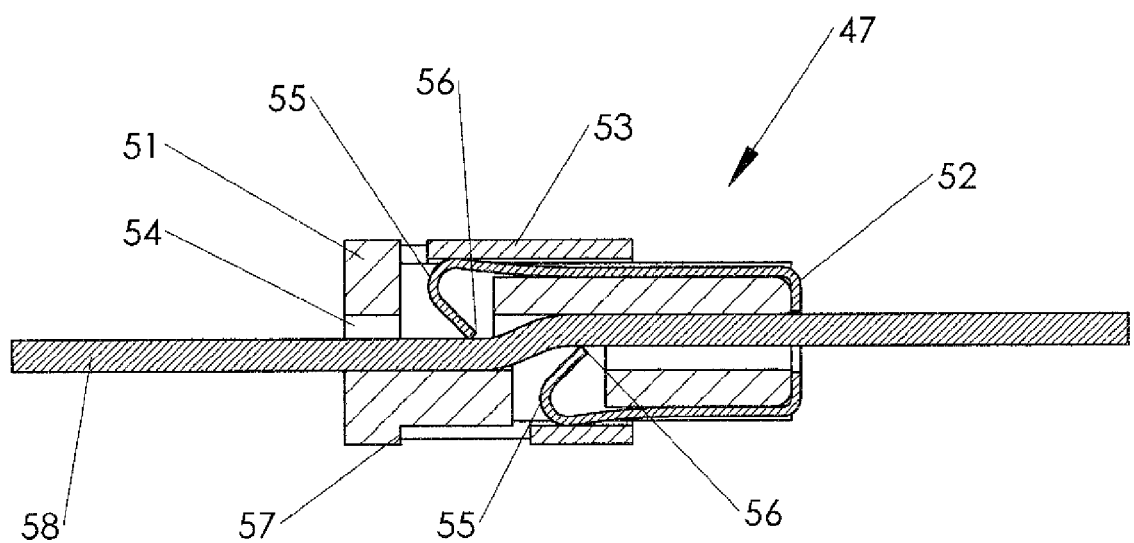
FIG. 38 is a cut-away view of a suture lock configured to lock onto suture.

FIGS. 36-38 illustrate a preferred embodiment of the suture lock 47. Other embodiments of suture locking devices which are known in the art are within the scope of this invention. FIG. 36 shows a perspective view of suture lock 47. Suture lock 47 is composed of three components, namely body 51, clip 52 and cylinder 53. In a preferred embodiment body 51 is constructed from polyacetal, clip 52 is composed of titanium, and cylinder 53 is composed of titanium. In alternate embodiments body 51, clip 52 and/or cylinder 53 may be constructed from stainless steel, polyacetal, polypropylene, polyethylene, PEEK, polylactic acid, polyglycolic acid, or any other metal, non-absorbable plastic, bioabsorbable plastic or biocompatible ceramic material known in the art.

Body 51 includes hole 54 which passes completely through body 51 and through a portion of clip 52. Suture 58 is shown passing through hole 54 in body 51. For illustrative simplicity one suture strand is shown in FIGS. 36-38, however suture lock 47 has the ability to slide over and then lock onto multiple strands of suture.

FIGS. 37 and 38 both show cut-away views of suture lock 47. In FIG. 37 suture lock 47 is in a first state in which it is configured to slideably engage with suture 58, and in FIG. 38 suture lock 47 is in a second state in which it is configured to lock onto suture 58. In use, suture 58 is passed through hole 54 of body 51. In FIG. 37 cylinder 53 is in a retracted position, which is towards the right side in this figure. In this retracted position bent portions 55 of clip 52 are able to spring outward, away from hole 54 and suture 58. In this configuration suture lock 47 is slideably engaged with suture 58, as tips 56 of clip 52 do not protrude into hole 54 far enough to interfere with suture 58. In FIG. 38 cylinder has been advanced over bent portions 55 of clip 52, which is towards the left in this figure. Cylinder 53 is advanced until it hits flange 57 of body 51. In this configuration cylinder 53 forces bent portions 55 of clip 52 inward, such that tips 56 of clip 52 are forced inward and clamp suture 58 between tips 56 of clip 52 and the wall of hole 54. A delivery device 48 (a portion of which is shown in FIGS. 31 and 32) is used to advance suture lock 47 along suture 58 when suture lock 47 is in the first state in which it is slideably engaged with suture 58. Delivery device 48 is also used to advance cylinder 53 relative to body 51 and clip 52 to achieve the second state in which suture lock 47 is configured to lock onto suture 58.

The new and novel method of manipulating the wall of a hollow organ and fixating two or more regions of the wall of the hollow organ to each other which is enabled by this invention combines the advantages of open, laparoscopic and endoscopic treatments, without any of the disadvantages of these treatments. These advantages will now be reviewed. The use of the invention to treat the stomach will continue to be used as an illustrative example, however these advantages apply to the use of the invention in other hollow organs. Specifically, the invention:

allows large areas of stomach tissue to be easily manipulated, as the design of instrument 10 provides great flexibility in the placement of the fixation locations;

allows access to and fixation of the external wall of the stomach (serosa);

results in no cosmetic scarring, as the procedure is performed via a gastroscopic approach;

minimizes post-operative adhesions, as no tissue is cut or dissected to perform the procedure, other than the creation of a small hole in the wall of the organ at each of the fixation locations;

minimizes post-procedure pain, as a minimum of tissue is disrupted;

enables fast post-procedure recovery, due to the gastroscopic approach;

allows the possibility of performing the procedure with the patient under sedation rather than general anesthesia, due to the gastroscopic approach;

brings multiple regions of the outer surface of the stomach into apposition with one another;

provides a high degree of efficacy, as the design of the instrument allows the regions of the stomach wall that are brought into apposition and fixated to be located in positions that optimize efficacy, such as close to the gastroesophageal junction, and/or a great distance apart from one another;

does not require loads to be applied at an angle from the central axis of the device, as the load to create the fold in the tissue is applied along the length of a suture;

utilizes an apparatus which does not lock onto the tissue at any point during the procedure, as instrument 10 may be safely and easily withdrawn and removed at any point throughout the procedure;

does not require surgical intervention in the event of a device malfunction, as instrument 10 may be safely and easily withdrawn and removed at any point throughout the procedure;

includes of simple, inexpensive, disposable equipment;

does not require hinged components;

has a high degree of reliability;

includes devices with small cross-sectional areas, allowing the entire procedure to be performed through the working channel of a flexible endoscope;

does not limit the location of the points of engagement with the tissue;

allows points of tissue that are far from each other to be engaged and brought into apposition; and ensures that structures outside of the stomach are not involved in the tissue engagement or fixation, as piercing element 15 is only advanced through the wall of the stomach.

As discussed previously, this invention may also treat other conditions in the stomach or elsewhere in the digestive tract, such as the small or large intestines, or the gall bladder. This invention may be used to engage and fixation regions of multiple organs to each other, such as the small intestine to the stomach, for example. This invention may also have application in other hollow organs, such as for example the urinary bladder, heart or lungs.

While the invention has been described in detail with reference to the preferred embodiments thereof, it will be apparent to one skilled in the art that various changes and modifications can be made and equivalents employed, without departing from the present invention. Although specific embodiments are presented herein, variations which could be anticipated by one who is knowledgeable or skilled in the art are considered within the scope of the specification and claims.

What is claimed is:

1. A method of creating and fixating a fold in a wall of a hollow organ, the method comprising:

selecting a first tube having a lumen, a proximal end, and a distal end, and placing the distal end of the first tube within the inside of the organ;

selecting an elongated second tube having a lumen, a proximal end, and an articulating section terminating in a distal end having a location indicator, and placing the elongated tube through the lumen of the first tube into the interior of the tissue, the elongated tube being rotatable relative to the first tube;

passing a piercing element through the lumen of the elongated tube to pierce the wall of the hollow organ at a first location from the inside of the organ to the outside of the organ to create a first hole in the wall of the organ;

advancing the elongated tube through the first hole in the wall of the organ;

positioning the distal end of the elongated tube near the outer wall of the organ at a desired second location, spaced from the first location, by articulating the articulating section of the elongated tube and rotating the elongated tube as desired;

optically detecting from within the organ the position of the distal end of the elongated tube;

after the distal end of the elongated tube is optically detected to be at the desired second location, piercing the wall of the organ at the second location from the outside of the organ to the inside of the organ to create a second hole in the wall of the organ;

delivering a first tissue anchor and a suture through the first and second holes in the wall of the organ, the suture being attached to the first tissue anchor;

delivering a second tissue anchor over the suture and advancing the second tissue anchor over the suture, thereby moving the first and second holes in the wall of the organ towards one another and bringing multiple regions of the outer surface of the organ into apposition; and locking the second tissue anchor onto the suture.

2. The method of claim 1 wherein positioning the distal end of the elongated tube includes activating a light source associated with the distal end of the elongated tube.

3. The method of claim 1 wherein positioning the distal end of the elongated tube includes retracting the piercing element relative to the distal end of the elongated tube to minimize damage to structures outside of the organ.

4. The method of claim 1 wherein piercing includes applying electrical energy to cauterize the tissue.

5. The method of claim 1 further including:
selecting an inner tube configured to pass through the lumen of the elongated tube, the inner tube having a second lumen, a proximal end, and a distal end; and
advancing the inner tube back into the organ through the second hole.

6. A method of creating and fixating a fold in a wall of a hollow organ, the method comprising:
selecting a first tube having a lumen, a proximal end, and a distal end, and placing the distal end of the first tube within the inside of the organ;
selecting an elongated second tube having a lumen, a proximal end, and an articulating section terminating in a distal end having a location indicator, and placing the elongated tube through the lumen of the first tube into the interior of the tissue, the elongated tube being rotatable relative to the first tube;
passing a piercing element through the lumen of the elongated tube to pierce the wall of the hollow organ at a first location from the inside of the organ to the outside of the organ to create a first hole in the wall of the organ;
advancing the elongated tube through the first hole in the wall of the organ;
retracting the piercing element relative to the distal end of the elongated tube, during movement of the distal end after it is advanced through the first hole, to minimize damage to structures outside of the organ;
positioning the distal end of the elongated tube near the outer wall of the organ at a desired second location, spaced far from the first location, by articulating the articulating section of the elongated tube and rotating the elongated tube as desired, and activating a visible light source associated with the distal end;
optically detecting from within the organ the position of the distal end of the elongated tube by viewing visible light from the light source; and
after the distal end of the elongated tube is optically detected to be at the desired second location, piercing the wall of the organ at the second location from the outside of the organ to the inside of the organ to create a second hole in the wall of the organ.

7. The method of claim 6 further including:
selecting an inner tube configured to pass through the lumen of the elongated tube, the inner tube having a second lumen, a proximal end, and a distal end; and
advancing the inner tube back into the organ through the second hole.

8. The method of claim 7 further including:
delivering a first tissue anchor and a suture through the first and second holes in the wall of the organ by passing the first tissue anchor and the suture through the second lumen of the inner tube, the suture being attached to the first tissue anchor; and
delivering a second tissue anchor over the suture and advancing the second tissue anchor over the suture, thereby moving the first and second holes in the wall of the organ towards one another and bringing multiple regions of the outer surface of the organ into apposition; and
locking the second tissue anchor onto the suture.

* * * * *